(12) United States Patent
Fujieda et al.

(10) Patent No.: US 8,796,246 B2
(45) Date of Patent: Aug. 5, 2014

(54) 9,10-SECOPREGNANE DERIVATIVE AND PHARMACEUTICAL

(75) Inventors: Hiroki Fujieda, Kobe (JP); Hironori Otsu, Matsubara (JP); Shoji Yasufuku, Otsu (JP); Masaaki Shirai, Kyoto (JP)

(73) Assignee: Nippon Shinyaku Co., Ltd., Kyoto (JP)

( * ) Notice: Subject to any disclaimer, the term of this patent is extended or adjusted under 35 U.S.C. 154(b) by 682 days.

(21) Appl. No.: 12/302,975

(22) PCT Filed: Jun. 1, 2007

(86) PCT No.: PCT/JP2007/061221
§ 371 (c)(1),
(2), (4) Date: Sep. 16, 2009

(87) PCT Pub. No.: WO2007/142158
PCT Pub. Date: Dec. 13, 2007

(65) Prior Publication Data
US 2010/0016263 A1 Jan. 21, 2010

(30) Foreign Application Priority Data
Jun. 2, 2006 (JP) ................................. 2006-155465

(51) Int. Cl.
*A61K 31/593* (2006.01)
*C07C 401/00* (2006.01)

(52) U.S. Cl.
USPC .......................................... 514/167; 552/653

(58) Field of Classification Search
USPC .......................................... 514/167; 552/653
See application file for complete search history.

(56) References Cited

U.S. PATENT DOCUMENTS

| | | | |
|---|---|---|---|
| 5,612,325 A | 3/1997 | Hansen et al. | |
| 5,756,733 A | 5/1998 | Hesse et al. | |
| 6,296,997 B1 | 10/2001 | Romanet et al. | |
| 7,074,777 B2 * | 7/2006 | Kawase et al. | 514/167 |
| 2002/0032340 A1 | 3/2002 | Kawase | |
| 2003/0195176 A1 * | 10/2003 | Kawase et al. | 514/167 |
| 2004/0019023 A1 | 1/2004 | Morikawa et al. | |

FOREIGN PATENT DOCUMENTS

| | | |
|---|---|---|
| EP | 0184112 | 6/1986 |
| JP | 08-509971 A | 10/1996 |
| JP | 10-231284 A | 9/1998 |
| JP | 2908566 B | 6/1999 |
| WO | WO-96/22776 | 8/1996 |
| WO | WO-2006/059768 A1 | 6/2006 |

OTHER PUBLICATIONS

Kobayashi, et al., 1998. Nishinihon-hihuka 60: 882.
Kondo, et al., 2000. "Comparative inhibitory effects of vitamin $D_3$ and an analogue on normal and psoriatic epidermis in organ culture." Arch Dermatol Res 292: 550-555.
Kobayashi, et al., 1995. "Growth inhibition of human keratinocytes by MC903 (calcipotriol) is linked to dephosphorylation of retinoblastoma gene product." Journal of the European Acadamy of Dermatology and Venereology 5: 132-138.
Kragballe, K., and Wildfang, I. L., 1990. "Calcipotriol (MC903), a novel vitamin $D_3$ analogue stimulates terminal differentiation and inhibits proliferation of cultured human keratinocytes." Arch Dermatol Res 282: 164-167.
Matsunaga, et al., 1990. "1,24(R)-Dihydroxyvitamin $D_3$ , a Novel Active Form of Vitamin $D_3$ with High Activity for Inducing Epidermal Differentiation but Decreased Hypercalcemic Activity." Journal of Dermatology 17: 135-142.
Takahashi, et al., 2003. "Similarly potent action of 1,25-dihydroxyvitamin $D_3$ and its analogues, tacalcitol, calcipotriol, and maxacalcitol on normal human keratinocyte proliferation and differentiation." Journal of Dermatological Science 31: 21-28.
Komine, et al., 1999. "The action of a novel vitamin $D_3$ analogue, OCT, on immunomodulatory function of keratinocytes and lymphocytes." Arch Dermatol Res 291: 500-506.

(Continued)

*Primary Examiner* — Sabiha N Qazi
(74) *Attorney, Agent, or Firm* — McDermott Will & Emery LLP

(57) ABSTRACT

A main object of the invention is to provide a novel useful vitamin $D_3$ derivative, which has an excellent vitamin $D_3$ activity and, as compared with conventional vitamin $D_3$ derivatives, has a relatively small amount of influence on the systemic calcium metabolism. The invention includes a 9,10-secopregnane derivative of the following general formula [1] and a pharmaceutical composition containing it as active ingredient.

[Formula 1]

In the general formula [1], the following partial structure between the 16-position and the 17-position means a single bond or a double bond:

[Formula 2]

Y is a single bond, an alkylene, an alkenylene or phenylene; $R^1$ and $R^2$ are the same or different, each represents hydrogen, an alkyl or a cycloalkyl; or $R^1$ and $R^2$, taken together with the adjacent carbon atom, form a cycloalkyl; $R^3$ is hydrogen or methyl; Z is hydrogen, hydroxy or $-NR^{11}R^{12}$.

5 Claims, No Drawings

(56) References Cited

OTHER PUBLICATIONS

Kubodera, et al., 1991. "Synthetic Studies of Vitamin D Analogues. IX. Synthesis and Differentiation-Inducing Activity of 1∝,25-Dihydroxy-23-oxa-,thia-, and azavitamin $D_3$." Chem. Pharm. Bull. 39(12): 3221-3224.

Kubodera, et al., 1992. "Synthetic Studies of Vitamin D Analogues. XI. Synthesis and Differentiation-Inducing Activity of 1∝25-Dihydroxy-22-oxavitamin $D_3$ Analogues." Chem. Pharm. Bull. 40(6): 1494-1499.

Watanabe, et al., 1996. "Synthetic Studies of Vitamin D Analogs. XXII. Synthesis and Antiproliferation Activity of Putative Metabolites of 1∝,25-Dihydroxy-22-oxavitamin $D_3$." Chem. Pharm. Bull. 44(12): 2280-2286.

Allewaert, et al., 1994. "The biological activity of 23-oxa-,23-oxa-24-oxo-, and 23-thia-dihydroxyvitamin $D_3$." Steroids 59: 686-690.

Mizutani, et al., 2003. Iyaku Journal 39: 122-127.

Nakagawa, et al., 2003. Iyaku Journal 39: 93-97.

Inanaga, et al., 1979. "A Rapid Esterification by Means of Mixed Anhydride and Its Application to Large-ring Lactonization." Bull. Chem. Soc. Jpn. 52(7): 1989-1993.

Andersen, et al., 1992. "Identification and Synthesis of a Metabolite of KH 1060, A New Potent 1∝,25-Dihydroxyvitamin $D_3$ Analogue." Bioorganic & Medicinal Chemistry Letters 2(12): 1713-1716.

Shimizu, et al., 2004. "Synthesis of 21-nor-22-oxa-1∝,25-dihydroxyvitamin $D_3$ derivatives in quest of a drug with low calcemic activity." Tetrahedron Letters 45: 7837-7841.

Hepworth, Harry, 1919. "The Action of Girgnard Reagents on the Esters of Certain Dicarboxylic Acids." J. Chem. Soc. 115: 1203-1210.

Wu, et al., 2003. "A Tertiary Alcohol Analog of γ-Hydroxybutyric Acid as a Specific γHydroxybutyric Acid Receptor Ligand." Journal of Pharmacology and Experimental Therapeutics 305(2): 675-679.

Tordeux, et al., 1990. "Reactions of Trifluoromethyl Bromide and Related Halides: Part 9. Comparison between Additions and Carbonyl Compounds, Enamines, and Sulphur Dioxide in the Presence of Zinc." J. Chem. Soc. Perkin Trans. 1: 1951-1957.

Hatsui, et al., 1994. "Synthetic Photochemistry. LXII. The Photoaddition of 4-Methyl-2-oxo-γ-valerolactone to Cycloalkenes." Bull. Chem. Soc. Jpn. 67: 293-295.

Evans, et al., 1968. "Formation of Fluorinated Ethers in a Modified Halohydrin Reaction." J. Org. Chem. 33: 1839-1844.

Murayama, et al., 1986. "Synthetic Studies of Vitamin $D_3$ Analogues. VIII. Synthesis of 22- Oxavitamin $D_3$ Analogues." Chem. Pharm. Bull. 34(10): 4410-4413.

Sato, et al., 1980. "Effect of Wavelength on the Formation of 1∝-Hydroxyprevitamin $D_3$ in the Ultraviolet Irradiation of Cholesta-5,7-diene-1∝,3β-diol and Use of a Filter Solution in the Photochemical Reaction in the Synthesis of 1∝-Hydroxy-Vitamin $D_3$." J. Nutr. Sci. Vitaminol. 26: 545-556.

Ward, et al., 2001. "Probing Host-Selective Phytotoxicity: Synthesis of Destruxin B and Several Natural Analogues." J. Org. Chem. 66: 7832-7840.

Reetz, et al., 1986. "$CH_3Li/TiCl_4$: A Non-Basic and Highly Selective Grignard Analogue." Tetrahedron 42(11): 2931-2935.

Clark, J. Stephen, 1992. "Diastereoselective Synthesis of 2,5-Dialkyl Tetrahydrofuran-3-ones by a Copper Catalysed Tandem Carbenoid Insertion and Ylide Rearrangement Reaction." Tetrahedron Letters 33(41): 6193-6196.

Tanikaga, et al., 1983. "Facile Synthesis of 4-Hydroxy-(E)-2-alkenoic Esters from Aldehydes." Synthesis, pp. 134-135.

Durham, Timothy B., and Miller, marvin J., 2003. "Enantioselective Synthesis of ∝-Amino Acids from N-Tosyloxy β-Lactams Derived from β-Keto Esters." J. Org. Chem. 68: 27-34.

Moroe, et al., 1952. "Synthesis of Isocitronellol (Synthetic Perfume)." Yakugaku Zasshi 72: 1172-1174.

Gerald M. Rosen and Marvin J. Turner III, 1988. "Synthesis of Spin Traps Specific for Hydroxy Radical." J. Med. Chem. 31(2): 428-432.

Okamoto, et al., 1958. "Rates of Solvolysis of Phenyldimethylcarbinyl Chlorides Containing Meta Directing Substituents." J. Am. Chem. Soc. 80: 4969-4971.

Taylor, et al., 1998. "Spiro γ-Lactones via Aluminum Enolate-Spiroepoxide Openings." Synthesis 7: 1009-1014.

Sterling, et al., 1987. "Use of Malic Acid as a Chiral Synthon: 24,25-Dihydroxycholecalciferol." Tetrahedron Letters 28(15): 1685-1688.

Haynes, L. J., and Jones, E. R. H., 1946. "Researches on Acetylenic Compounds. Part V. ∝β-Acetylenic Hydroxy-acids." J. Chem. Soc., pp. 503-506.

Damon, et al., 1976. "A General Synthesis of 2-Alkyl Tetronic Acids." Tetrahedron Letters 32: 2749-2752.

Lehmann, Jochen, 1983. "Synthese dihydroxylierter Diphenylalkylamine uber Azalactone." Archiv der Phamazie 316: 339-346.

Lazar, Jospeh, and Sheppard, William A., 1968. Fluorinated Analogs of Leucine, Methionine, and Valine. J. Med. Chem. 11: 138-140.

Kasibhalta, et al., 2000. "AMP Deaminase Inhibitors. 3. SAR of 3-(Carboxyarylalkyl)coformycin Aglycon Analogues." J. Med. Chem. 43: 1508-1518.

Freidlin, et al., 1962. "Vinyl Monomers From Dicarboxylic Acids. I. Monoesters of Adipic and Succinic Acids." J. Gen. Chem. USSR (English Translation) 32: 786-788.

Johnson, David C., and Stratton, Belinda, 1987. "A Comparison of the Hammett Acidity Function Method for Determination of $pK_a$ Values with the Bunnett-Olsen and Excess Acidity Function Methods." J. Org. Chem. 52: 4798-4800.

Pator and Yus, 2001. "Masked β-, γ- δ-lithium ester enolates: useful reagents in organic synthesis." Tetrahedron Lett., 42, 1029-1032.

Prakash et al. 1989. "Fluoride-induced Trifluoromethylation of Carbonyl Compounds with Trifluoromethyltrimethylsilane (TMS-CF3). A Trifluoromethide Equivalent." J. Am. Chem. Soc., 111, 393-395 (1989).

Blaehr et al., 2003. "Synthesis of Novel Hapten Derivatives of 1 α, 25-Dihydroxy-vitamin D3 and Its 20-Epi Analogue." J. Org. Chem., 68, 1367-1375.

Perlman et al. 1991. "Novel Synthesis of 19-Nor-Vitamin D Compounds." Tetrahedron Lett., vol. 32, No. 52, pp. 7663-7666.

Sicinski et al. 1998. "New 1 α, 25-Difydroxy-19-norvitamin D3 Compounds of High Biological Activity: Synthesis and Biological Evaluation of 2-Hydroxymethyl, 2-Methyl, and 2-Methylene Analogues." J. Med. Chem., 41, 4662-4674.

Baggiolini et al. "Stereocontrolled Total Synthesis of 1α, 25-Dihydroxyxholecalciferol and 1α, 25-Dihydroxyergocalciferol." J. Org. Chem., 51, 3098-3108.

* cited by examiner

9,10-SECOPREGNANE DERIVATIVE AND PHARMACEUTICAL

This application is a U.S. national phase application under 35. U.S.C. §371of International Patent Application No. PCT/JP2007/061221, filed Jun. 1, 2007, and claims the benefit of Japanese Patent Application No. 2006-155465, filed Jun. 2, 2006. The International Application was published in Japanese on Dec. 13, 2007 as WO 2007/142158. The disclosures of all the prior applications are hereby incorporated by reference in their entireties.

TECHNICAL FIELD

The present invention relates to a 9,10-secopregnane derivative (vitamin $D_3$ derivative) and a pharmaceutical composition containing it as an active ingredient.

BACKGROUND ART

Psoriasis vulgaris, ichthyosis syndrome, keratosis of palm and sole, pustulosis of palm and sole and lichen pilaris are dyskeratosis in a broad sense showing various characteristic skin signs such as erythema, wetting, hypertrophy, keratinization and scale. This disease is an intractable chronic disease and causes a big obstacle to comfortableness of daily life of patients. With regard to its pathological background, it has been believed to be based on disorder of growth and differentiation of both inflammatory cells and skin cells.

Psoriasis vulgaris which is a representative disease of dyskeratosis is not fatal, but it is intractable and is accompanied by prejudice for its appearance and also by mental pain. Therefore, there are many cases where the quality of life (QOL) is deteriorated significantly.

Many therapeutic methods have been applied to the above-mentioned keratosis such as psoriasis vulgaris. There is, however, no radical therapy and symptomatic treatment and care over a long period of time have been performed. As a main therapeutic method, external application of adrenocorticosteroidal agents has been widely adopted achieving an excellent therapeutic effect. However, there is also a strong side effect and induction of skin atrophy and rebound has been considered to be a problem in particular.

In recent years, topical application of vitamin $D_3$ derivatives having a 9,10-secopregnane skeleton has been widely used. As compared with steroids, this topically applicable agent has fewer side effects and has an effect to prolong the term before the recurrence is noted (refer, for example, to Non-Patent Reference 1). It has been believed that the vitamin $D_3$ derivative is effective for keratosis including psoriasis vulgaris via a suppressive action on the growth of epidermal cells (refer, for example, to Non-Patent References 2and 3), a promotional action on epidermal cell differentiation (refer, for example, to Non-Patent References 4to 6), a suppressive action on cytokine production and a suppressive action on the activation of T cells (refer, for example, to Non-Patent Reference 7), etc.

With regard to a vitamin $D_3$ derivative having a 9,10-secopregnane skeleton, for example, there have been known various derivatives such as (1S,3R,20S)-20-(3-hydroxy-3-methylbutyloxy)-9,10-secopregna-5Z,7E,10(19)-trien-1,3-diol (generic name: maxacalcitol) (its synthetic method and pharmacological actions are mentioned, for example, in Patent Reference 1and its pharmacological actions are mentioned, for example, in Non-Patent References 8to 10), the compounds mentioned in Patent Reference 2. or Non-Patent Reference 11, etc.

On the other hand, it has been well known that $1\alpha,25(OH)_2 D_3$ which is an active form of vitamin D increases the level of serum calcium concentration together with the level of serum parathyroid hormone whereby calcium homeostasis is maintained and controlled. The most anxious side effects of vitamin $D_3$ derivatives which have been clinically used at present are dry mouth, malaise, torpor, anorexia, vomiting, abdominal pain and muscular weakness as a result of the increase in calcium concentration in serum (hypercalcemia). Accordingly, it is necessary to periodically measure the calcium concentration in blood not only in the case where administration is given to patients suffering from hypercalcemia but also in patients who are not suffering from the disease. There is also a limitation on its dose (refer, for example, to Non-Patent References 12and 13).

Consequently, there has been an earnest desire for a vitamin $D_3$ derivative which, as compared with conventional vitamin $D_3$ derivatives, has a relatively small amount of influence on the systemic calcium metabolism and is able to specifically relieve the dyskeratosis of epidermal cells, as a therapeutic agent for keratosis such as psoriasis vulgaris.

Patent Reference 1:EP-A 0184112
Patent Reference 2:Japanese Patent 2908566
Patent Reference 3:U.S. Pat. No. 6,296,997
Patent Reference 4:U.S. Pat. No. 5,612,325
Patent Reference 5:USP Application 2004-0019023
Patent Reference 6:JP-A-Hei-10-231284
Non-Patent Reference 1:Kobayashi J., et al., Nishinihon-hihuka, 60, 882(1998)
Non-Patent Reference 2:Kondo S., et al., Arch. Dermatol. Res., 292, 550(2000)
Non-Patent Reference 3:Kobayashi T., et al., J. Eur. Acad. Dermatol. Venereol., 5, 132(1995)
Non-Patent Reference 4:Kragballe K., et al., Arch. Dermatol. Res., 282, 164(1990)
Non-Patent Reference 5:Matunaga T., et al., J. Dermatol., 17, 135(1990)
Non-Patent Reference 6:Takahashi H., et al., J. Dermatol. Sci., 31, 21(2003)
Non-Patent Reference 7:Komine M., et al., Arch. Dermatol. Res., 291, 500(1999)
Non-Patent Reference 8:Chem. Pharm. Bull., 39(12), 3221-3224(1991)
Non-Patent Reference 9:Chem. Pharm. Bull., 40(6), 1494-1499(1992)
Non-Patent Reference 10:Chem. Pharm. Bull., 44(12), 2280-2286(1996)
Non-Patent Reference 11:Steroids, 59, 686(1994)
Non-Patent Reference 12:Mizutani J., Iyaku Journal, 39, 122 (2003)
Non-Patent Reference 13:Nakagawa H., Iyaku Journal, 39, 93 (2003)
Non-Patent Reference 14:Bull. Chem. Soc. Jpn., 52(7), 1989-1993(1979)
Non-Patent Reference 15:Chem. Pharm. Bull., 44, 2280 (1996)
Non-Patent Reference 16:Bioorg. Med. Chem. Lett., 2, 1713 (1992)
Non-Patent Reference 17:Tetrahedron Lett., 45, 7837(2004)
Non-Patent Reference 18:J. Chem. Soc., 115, 1207(1919)
Non-Patent Reference 19:J. of Pharmacology and Experimental Therapeutics, 305, 675(2003)
Non-Patent Reference 20:J. Chem. Soc. Perkin Trans. 1, 7, 1951(1990)
Non-Patent Reference 21:Bull. Chem. Soc. Jpn, 67, 293 (1994)
Non-Patent Reference 22:J. Org. Chem., 33, 1839. (1968)

Non-Patent Reference 23:Chem. Pharm. Bull., 34(10), 4410-4413(1986)
Non-Patent Reference 24:J. Nutr. Sci. Vitaminol., 26, 545-556(1980)
Non-Patent Reference 25:J. Org. Chem., 66(23), 7832-7840 (2001)
Non-Patent Reference 26:Tetrahedron, 42(11), 2931-2935 (1986)
Non-Patent Reference 27:Tetrahedron Lett., 33, 41; 6193-6196. (1992)
Non-Patent Reference 28:Synthesis, 134-135. (1983)
Non-Patent Reference 29:J. Org. Chem., 68(1), 27-34. (2003)
Non-Patent Reference 30:Yakugaku Zasshi, 72, 1172. (1952)
Non-Patent Reference 31:J. Med. Chem., 31(2), 428-32 (1988)
Non-Patent Reference 32:J. Chem. Soc., 115, 1207. (1919)
Non-Patent Reference 33:J. Am. Chem. Soc., 80, 4969-4971 (1958)
Non-Patent Reference 34:Tetrahedron., 42, 11, 2931-2935 (1986)
Non-Patent Reference 35:Tetrahedron., 42, 11, 2931-2935 (1986)
Non-Patent Reference 36:Synthesis, 7, 1009-1014(1998)
Non-Patent Reference 37:Tetrahedron Lett., 28(15), 1685-1688(1987)
Non-Patent Reference 38:J. Chem. Soc., 503-506(1946)
Non-Patent Reference 39:Tetrahedron Lett., 2749-2752 (1976)
Non-Patent Reference 40:Archiv der Phamazie, 316, 339-346 (1983)
Non-Patent Reference 41:J. Med. Chem., 11, 138-140(1968)
Non-Patent Reference 42:J. Med. Chem., 43, 1508-1518 (2000)
Non-Patent Reference 43:J. Gen. Chem. USSR (Engl. Transl.), 32, 786-788(1962)
Non-Patent Reference 44:J. Org. Chem., 52, 4798-4800 (1987)
Non-Patent Reference 45:Tetrahedron Lett., 42, 1029-1032 (2001)
Non-Patent Reference 46:J. Am. Chem. Soc., 111, 393-395 (1989)
Non-Patent Reference 47:J. Org. Chem., 68, 1367-1375 (2003)
Non-Patent Reference 48:Tetrahedron Lett., 32, 7663(1991)
Non-Patent Reference 49:J. Med. Chem., 4662-4674(1998)
Non-Patent Reference 50:J. Org. Chem., 51, 3098-3108 (1986)

DISCLOSURE OF THE INVENTION

Problems that the Invention is to Solve

A main object of the invention is to provide a novel and useful vitamin $D_3$ derivative which has an excellent vitamin $D_3$ activity and which, as compared with conventional vitamin $D_3$ derivatives, has a relatively small amount of influence on the systemic calcium metabolism.

Means for Solving the Problems

The present inventors have extensively conducted various investigations and found that a novel 9,10-secopregnane derivative which will be mentioned below or a pharmaceutically acceptable salt thereof achieved the above object and accomplished the invention.

The invention may include a 9,10-secopregnane derivative represented by the following general formula [1] (hereinafter, referred to as the compound of the invention) or a pharmaceutically acceptable salt thereof. A characteristic feature of the compound of the invention in terms of the structure thereof is that a carbonyloxy group is directly bound to the 20-positioned carbon not via an alkylene chain therebetween.

[Formula 1]

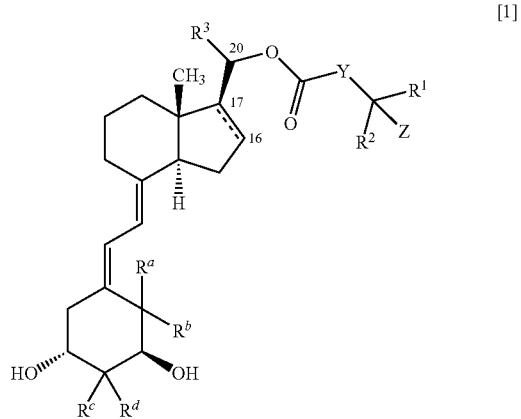

[1]

In the general formula [1],
the following partial structure between the 16-position and the 17-position means a single bond or a double bond:

[Formula 2]

Y represents (1) a single bond, (2) an alkylene having 1 to 5 carbon atoms and optionally substituted with 1 to 3 substituents selected from a group of halogen, hydroxy and oxo, (3) an alkenylene having 2 to 5 carbon atoms, or (4) phenylene.

$R^1$ and $R^2$ are the same or different, each represents (1) hydrogen, (2) an alkyl having 1 to 6 carbon atoms and optionally substituted with 1 to 3 halogens, or (3) a cycloalkyl having 3 to 8 carbon atoms; or $R^1$ and $R^2$, taken together with the adjacent carbon atom, form a cycloalkyl having 3 to 8 carbon atoms.

$R^3$ represents hydrogen or methyl.

Z represents hydrogen, hydroxy or $-NR^{11}R^{12}$. $R^{11}$ represents hydrogen or an alkyl having 1 to 6 carbon atoms; $R^{12}$ represents (1) an alkyl having 1 to 6 carbon atoms and optionally substituted with hydroxy, or (2) an alkylsulfonyl having 1 to 6 carbon atoms.

$R^a$ and $R^b$ are both hydrogens, or $R^a$ and $R^b$, taken together, form methylene.

$R^c$ and $R^d$ are the same or different, each represents hydrogen or methyl, or $R^c$ and $R^d$, taken together, form methylene.

However, compounds where (1) $R^a$ and $R^b$, taken together, form methylene, (2) $R^c$ and $R^d$ are hydrogens, and (3) the partial structure between the 16-position and the 17-position is a single bond are excluded.

The invention also includes a pharmaceutical composition containing a compound of the invention or a pharmaceutically acceptable salt thereof as an active ingredient, or a therapeutic agent for dyskeratosis including psoriasis vulgaris that comprises a compound of the invention or a pharmaceutically acceptable salt thereof as an active ingredient.

Of the compounds of the invention, for example, preferred are the following compounds (1) to (35):

(1) (1S,3R,20S)-20-(4-hydroxy-4-methylpentanoyloxy)-9,10-secopregna-5Z,7E,10(19),16-tetraene-1,3-diol,
(2) (1R,3R,20S)-19-nor-20-(4-hydroxy-4-methylpentanoyloxy)-9,10-secopregna-5Z,7E-diene-1,3-diol,
(3) (1R,3R,20S)-2-methylene-19-nor-20-(4-hydroxy-4-methylpentanoyloxy)-9,10-secopregna-5Z,7E-diene-1,3-diol,
(4) (1R,3R,20S)-19-nor-20-[(2E)-4-ethyl-4-hydroxyhex-2-enoyloxy]-9,10-secopregna-5Z,7E-diene-1,3-diol,
(5) (1R,3R,20S)-19-nor-20-(5,5,5-trifluoro-4-hydroxy-4-methylpentanoyloxy)-9,10-secopregna-5Z,7E-diene-1,3-diol,
(6) (1R,3R,20S)-2-methylene-19-nor-20-(5,5,5-trifluoro-4-hydroxy-4-methylpentanoyloxy)-9,10-secopregna-5Z,7E-diene-1,3-diol,
(7) (1R,3R,20S)-2-methylene-19-nor-20-[(2E)-4-ethyl-4-hydroxyhex-2-enoyloxy]-9,10-secopregna-5Z,7E-diene-1,3-diol,
(8) (1R,3R,20S)-19-nor-20-(4-hydroxy-4-methylpentanoyloxy)-9,10-secopregna-5Z,7E,16-triene-1,3-diol,
(9) (1R,3R,20S)-19-nor-20-(5,5,5-trifluoro-4-hydroxy-4-methylpentanoyloxy)-9,10-secopregna-5Z,7E,16-triene-1,3-diol,
(10) (1R,3R,20S)-19-nor-2-methylene-20-(4-hydroxy-4-methylpentanoyloxy)-9,10-secopregna-5Z,7E,16-triene-1,3-diol,
(11) (1S,3R,20S)-20-(5,5,5-trifluoro-4-hydroxy-4-methylpentanoyloxy)-9,10-secopregna-5Z,7E,10(19),16-tetraene-1,3-diol,
(12) (1R,2α,3R,20S)-2-methyl-19-nor-20-(4-hydroxy-4-methylpentanoyloxy)-9,10-secopregna-5Z,7E-diene-1,3-diol,
(13) (1R,2β,3R,20S)-2-methyl-19-nor-20-(4-hydroxy-4-methylpentanoyloxy)-9,10-secopregna-5Z,7E-diene-1,3-diol,
(14) (1R,3R,20S)-2-methyl-19-nor-20-(5,5,5-trifluoro-4-hydroxy-4-methylpentanoyloxy)-9,10-secopregna-5Z,7E-diene-1,3-diol,
(15) (1R,3R,20S)-2-methyl-19-nor-20-[(2E)-4-ethyl-4-hydroxyhex-2-enoyloxy]-9,10-secopregna-5Z,7E-diene-1,3-diol,
(16) (1R,3R,20S)-19-nor-2-methyl-20-(4-hydroxy-4-methylpentanoyloxy)-9,10-secopregna-5Z,7E,16-triene-1,3-diol,
(17) (1R,3R,20S)-19-nor-2-methylene-20-[(4S)-5,5,5-trifluoro-4-hydroxy-4-methylpentanoyloxy]-9,10-secopregna-5Z,7E,16-triene-1,3-diol,
(18) (1R,3R,20S)-19-nor-2-methylene-20-[(4R)-5,5,5-trifluoro-4-hydroxy-4-methylpentanoyloxy]-9,10-secopregna-5Z,7E,16-triene-1,3-diol,
(19) (1R,3R,20S)-2-methylene-19-nor-20-(5-hydroxy-5-methylhexanoyloxy)-9,10-secopregna-5Z,7E-diene-1,3-diol,
(20) (1R,2α,3R,20S)-2-methyl-19-nor-20-(5-hydroxy-5-methylhexanoyloxy)-9,10-secopregna-5Z,7E-diene-1,3-diol,
(21) (1R,2β,3R,20S)-2-methyl-19-nor-20-(5-hydroxy-5-methylhexanoyloxy)-9,10-secopregna-5Z,7E-diene-1,3-diol,
(22) (1R,2α,3R,20S)-2-methyl-19-nor-20-(5,5,5-trifluoro-4-hydroxy-4-methylpentanoyloxy)-9,10-secopregna-5Z,7E-diene-1,3-diol,
(23) (1R,2β,3R,20S)-2-methyl-19-nor-20-(5,5,5-trifluoro-4-hydroxy-4-methylpentanoyloxy)-9,10-secopregna-5Z,7E-diene-1,3-diol,
(24) (1R,2α,3R,20S)-19-nor-2-methyl-20-(4-hydroxy-4-methylpentanoyloxy)-9,10-secopregna-5Z,7E,16-triene-1,3-diol,
(25) (1R,2β,3R,20S)-19-nor-2-methyl-20-(4-hydroxy-4-methylpentanoyloxy)-9,10-secopregna-5Z,7E,16-triene-1,3-diol,
(26) (1R,2α,3R,20S)-2-methyl-19-nor-20-[(2E)-4-ethyl-4-hydroxyhex-2-enoyloxy]-9,10-secopregna-5Z,7E-diene-1,3-diol,
(27) (1R,2β,3R,20S)-2-methyl-19-nor-20-[(2E)-4-ethyl-4-hydroxyhex-2-enoyloxy]-9,10-secopregna-5Z,7E-diene-1,3-diol,
(28) (1R,2α,3R,20S)-2-methyl-19-nor-20-[4-ethyl-4-hydroxyhexanoyloxy]-9,10-secopregna-5Z,7E-diene-1,3-diol,
(29) (1R,2β,3R,20S)-2-methyl-19-nor-20-[4-ethyl-4-hydroxyhexanoyloxy]-9,10-secopregna-5Z,7E-diene-1,3-diol,
(30) (1R,3R,20S)-19-nor-20-[(4S)-5,5,5-trifluoro-4-hydroxy-4-methylpentanoyloxy]-9,10-secopregna-5Z,7E,16-triene-1,3-diol,
(31) (1R,3R,20S)-19-nor-20-[(4R)-5,5,5-trifluoro-4-hydroxy-4-methylpentanoyloxy]-9,10-secopregna-5Z,7E,16-triene-1,3-diol,
(32) (1S,3R,20S)-20-[(4R)-5,5,5-trifluoro-4-hydroxy-4-methylpentanoyloxy]-9,10-secopregna-5Z,7E,10(19),16-tetraene-1,3-diol,
(33) (1S,3R,20S)-20-[(4S)-5,5,5-trifluoro-4-hydroxy-4-methylpentanoyloxy]-9,10-secopregna-5Z,7E,10(19),16-tetraene-1,3-diol,
(34) (1R,3R,20S)-19-nor-20-[(4S)-5,5,5-trifluoro-4-hydroxy-4-methylpentanoyloxy]-9,10-secopregna-5Z,7E-diene-1,3-diol,
(35) (1R,3R,20S)-19-nor-20-[(4R)-5,5,5-trifluoro-4-hydroxy-4-methylpentanoyloxy]-9,10-secopregna-5Z,7E-diene-1,3-diol.

The invention also includes a compound of the following (1) to (5) or a pharmaceutically acceptable salt thereof, a pharmaceutical composition containing a compound of the following (1) to (5) or a pharmaceutically acceptable salt thereof as an active ingredient, or a therapeutic agent for dyskeratosis including psoriasis vulgaris that comprises a compound of the following (1) to (5) or a pharmaceutically acceptable salt thereof as an active ingredient.

(1) (1S,3R,20S)-20-(5-hydroxy-5-ethylheptanoyloxy)-9,10-secopregna-5Z,7E,10(19)-triene-1,3-diol,
(2) (1S,3R,20S)-20-[(4R)-5,5,5-trifluoro-4-hydroxy-4-methylpentanoyloxy]-9,10-secopregna-5Z,7E,10(19)-triene-1,3-diol,
(3) (1S,3R,20S)-20-[(4S)-5,5,5-trifluoro-4-hydroxy-4-methylpentanoyloxy]-9,10-secopregna-5Z,7E,10(19)-triene-1,3-diol,
(4) (1S,3R,20S)-20-(6,6,6-trifluoro-5-hydroxy-5-methylhexanoyloxy)-9,10-secopregna-5Z,7E,10(19)-triene-1,3-diol,
(5) (1S,3R,20S)-20-(5,5,5-trifluoro-4-hydroxy-4-methyl-3-oxopentanoyloxy)-9,10-secopregna-5Z,7E,10(19)-triene-1,3-diol.

The invention is described in detail hereinunder.

"Halogen" in the invention includes, for example, fluorine, chlorine, bromine, iodine.

"Alkylene" in the invention is a linear or branched one having 1to 5carbon atoms, including, for example, methylene, ethylene, trimethylene, methylethylene, tetramethylene, methyltrimethylene, ethylethylene, pentamethylene, methyltetramethylene, ethyltrimethylene. In particular, preferred is a linear alkylene having 1to 3 carbon atoms. Alkylene in the invention may be substituted with 1to 3substituents selected from a group consisting of halogen, hydroxy and oxo.

"Alkenylene" in the invention is a linear or branched one having 2to 5carbon atoms. For example, it includes ethenylene, propenylene, butenylene, pentenylene. In particular, preferred is a linear alkenylene having 2to 4 carbon atoms.

"Phenylene" in the invention includes, for example, 1,2-phenylene, 1,3-phenylene, 1,4-phenylene.

"Alkyl" in the invention is a linear or branched one having 1to 6carbon atoms, including, for example, methyl, ethyl, n-propyl, isopropyl, n-butyl, isobutyl, sec-butyl, tert-butyl, n-pentyl, isopentyl, n-hexyl, isohexyl. Especially preferred are methyl and ethyl. Alkyl in the invention may be substituted with 1to 3halogens.

"Cycloalkyl" in the invention is, for example, a mono- to tricyclic alkyl having 3to 8carbon atoms, specifically including cyclopropyl, cyclobutyl, cyclopentyl, cyclohexyl, cycloheptyl, cyclooctyl, cyclononyl, cyclodecanyl, adamantyl (1-adamantyl, 2-adamantyl, etc.), 2-bicyclo[3.1.1]heptyl and 2-bicyclo[2.2.1]heptyl. In particular, preferred is a mono- to tricyclic alkyl having 4to 6carbon atoms.

Not specifically defined, the protective group for "hydroxy" in the invention may be any hydroxy-protective group usable in the reaction, including, for example, 1) a trialkylsilyl such as triethylsilyl, tributylsilyl, tert-butyldimethysilyl, etc.; 2) (2-trimethylsilyl)ethoxymethyl, 3) an aromatic methyl such as benzyl, 4-methoxyphenylmethyl, etc.; 4) an acyl such as acetyl, etc.; and 5) 2-tetrahydropyranyl.

BEST MODE FOR CARRYING OUT THE INVENTION

The compound of the invention may be produced from a known compound or from an easily synthesizable intermediate, for example, according to the method mentioned below. In production of the compound of the invention, in case where the starting material has a substituent having an influence on the reaction, in general, the starting material is previously protected with a suitable protective group according to a known method and then reacted. The protective group may be removed after the reaction according to a known method.

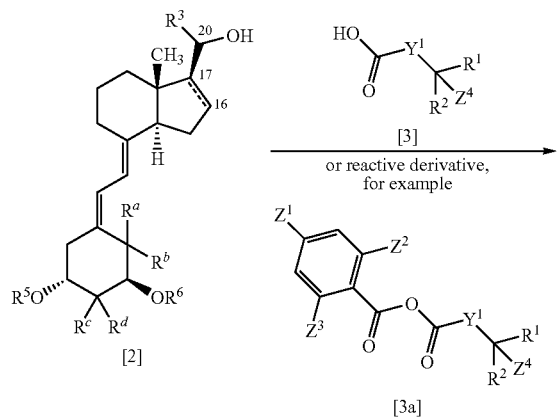

[Formula 3]

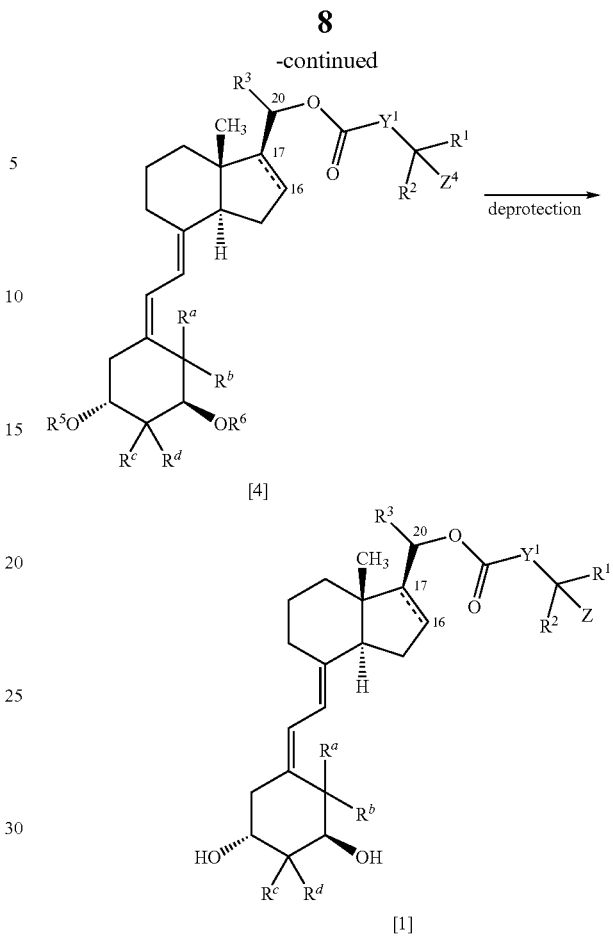

[In the formula, Y, Z, $R^1$, $R^2$, $R^3$, $R^a$, $R^b$, $R^c$. and $R^d$have the same meanings as above. $Y^1$represents (1) a single bond, (2) an alkylene having 1to 5carbon atoms and optionally substituted with 1to 3. substituents selected from a group consisting of halogen, protected hydroxy and oxo, (3) an alkenylene having 1to 5carbon atoms, or (4) phenylene. $R^5$and $R^6$each represent a protective group for hydroxy. $Z^1$, $Z^2$and $Z^3$are the same or different, each represents halogen, nitro or cyano. $Z^4$represents (1) hydrogen, (2) a protected hydroxy, or (3) —$NR^{13}R^{14}$$R^{13}$represents a hydrogen, or an alkyl having 1. to 6carbon atoms; $R^{14}$ represents (1) an alkyl having 1. to 6and optionally substituted with a protected hydroxy, or (2) an alkylsulfonyl having 1. to 6carbon atoms.]

This reaction is condensation of a compound (alcohol) of the general formula [2] and a compound (carboxylic acid) of the general formula [3] followed by deprotection, and therefore it may be accomplished according to a method per se as condensation and deprotection. For example, the above alcohol is reacted with the above carboxylic acid and then deprotected, thereby producing a compound of the invention.

First Step (Condensation)

This step is for condensation of the alcohol [2] and the carboxylic acid [3] at a reaction temperature of −20to 100° C., in the presence or absence of a base (for example, organic base such as triethylamine, N,N-diisopropyl-N-ethylamine, N,N-diethylaniline, pyridine, 4-dimethylaminopyridine and 1,8-diazabicyclo[5.4.0]undec-7-ene), using a condensing agent (for example, 1,1'-oxalyldiimidazole, 1-ethyl-3-(3-dimethylaminopropyl)carbodiimide, dicyclohexylcarbodiimide, diethyl cyanophosphonate, diphenylphosphorylazide and 2-chloro-1-methylpyridinium iodide). Not specifically defined, any solvent not participating in the reaction is usable, including, for example, ethers such as tetrahydrofuran, diethyl ether, etc.; amides such as N,N-dimethylformamide, N,N-dimethylacetamide, etc.; nitrites such as acetonitrile, propionitrile, etc.; hydrocarbons such as benzene, toluene, etc.; halogenohydrocarbons such as chloroform, dichloromethane, etc.; or their mixed solvents. In this step, an additive (for example, 1-hydroxybenzotriazole, N-hydroxysuccinimide, etc.) may be added.

The reaction time varies depending on the type of the starting materials and the condensing agents, the reaction temperature and others, but in general, it is suitably from 30. minutes to 24 hours. The amount of the above carboxylic acid [3] and that of the condensing agent are preferably from 1 to 3. molar times relative to the alcohol [2].

In place of the above carboxylic acid [3] for use in this step, also usable is its reactive derivative. The reactive derivative includes those generally used in ester-forming condensation, for example, acid halides (for example, acid chlorides and acid bromides), mixed acid anhydrides, imidazolides, active amides, etc. When the reactive derivative is used in the reaction, the above condensing agent may be omitted.

For example, in case where a mixed acid anhydride is used as the reactive derivative of the carboxylic acid [3], a pyridine solvent such as pyridine, 4-methylpyridine or the like or the same base and solvent as above are used and the condensation may be accomplished at a reaction temperature of −20 to 100° C. As the additive, for example, 4-dimethylaminopyridine may be added. The reaction time varies depending on the type of the mixed acid anhydride to be used and the reaction temperature, but in general, it is suitable from 30 minutes to 24 hours. In the step of using the mixed acid anhydride, the mixed acid anhydride is preferred to be a mixed acid anhydride of the following general formula [3a] (for example, refer to Non-Patent Reference 14).

[Formula 4]

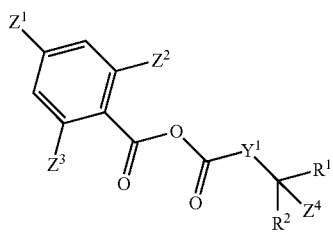

[3a]

[In the formula, $Y^1$, $R^1$, $R^2$, $Z^1$, $Z^2$, $Z^3$ and $Z^4$. have the same meanings as above.]

$R^5$ and $R^6$ are not specifically defined, and may be any hydroxy-protective group usable in the reaction. For example, they include the above-mentioned protective groups.

The starting compound of the general formula [2] may be produced according to a known method (for example, refer to Patent Reference 5, and Non-Patent References 15 to 17), or a similar method, or according to the method described in Examples given hereinunder.

The starting compound of the general formula [3] may be produced, for example, according to the same method as in Non-Patent References 18 to 22, or according to a method similar to the method described in Patent Reference 4 or Non-Patent References 26 to 41.

Second Step (Deprotection)

This step is hydroxy deprotection, and may be accomplished according to a per se ordinary method. Specifically, though varying depending on the type of the protective group used, when tert-butyldimethylsilyl is used as the protective group, it may be deprotected in the manner mentioned below.

For deprotection of the compound of the general formula [4], a deprotecting agent (for example, tetrabutylammonium fluoride, hydrogen fluoride, hydrogen fluoride-pyridine, acetic acid and trifluoroacetic acid) may be used, and the deprotection may be accomplished at a reaction temperature of from −20 to 100° C. Not specifically defined, any solvent not participating in the reaction may be used, including, for example, ethers such as tetrahydrofuran, diethyl ether, etc.; amides such as N,N-dimethylformamide, N,N-dimethylacetamide, etc.; nitrites such as acetonitrile, propionitrile, etc.; hydrocarbons such as benzene, toluene, etc.; halogenohydrocarbons such as chloroform, dichloromethane, etc.; or their mixed solvents. The reaction time varies depending on the type of the starting material and the deprotecting agent, but in general, it is suitably from 30 minutes to 24 hours. The amount of the deprotecting agent to be used is preferably from 1 to 100 molar times relative to the compound of the general formula [4].

The compound of the invention includes those having an asymmetric carbon, and the invention includes not only its optically active compounds but also its racemic compounds. In producing such optically active compounds, employable is an ordinary method of resolution with a chiral column; however, they may also be produced through asymmetric synthesis of the starting compound [2] (for example, they may be produced in the same manner as the asymmetric production method in Non-Patent References 15 and 16).

In case where the compound of the invention includes geometric isomers or tautomers, not only any one isomer of them but also their mixtures are within the scope of the compound of the invention.

The compound of the invention may be used as a pharmaceutical directly as it is in the form of a free base, but may be used after being formed into a pharmaceutically acceptable salt according to a known method. The salt includes salts with a mineral acid such as hydrochloric acid, hydrobromic acid, sulfuric acid, phosphoric acid, etc.; or salts with an organic acid such as acetic acid, citric acid, tartaric acid, maleic acid, succinic acid, fumaric acid, p-toluenesulfonic acid, benzenesulfonic acid, methanesulfonic acid, etc.

For example, hydrochlorides of the compound of the invention may be obtained by dissolving the compound of the invention in an alcohol solution, ethyl acetate solution or ether solution of hydrogen chloride.

The compound of the invention is useful as a pharmaceutical, as shown in Test Examples given hereinunder, and is especially useful as a therapeutic agent for dyskeratosis including psoriasis vulgaris.

In case where the compound of the invention is administered as a pharmaceutical, the compound of the invention may be administered to mammals including humans, directly as it is or in the form of a pharmaceutical composition containing it in a pharmaceutically acceptable and nontoxic inert carrier in an amount of, for example, from 0.0001 to 99.5%, preferably from 0.001 to 90%.

The carrier may be at least one of solid, semisolid or liquid diluents, fillers and other formulation aids. The pharmaceutical composition is preferably administered in the form of a dose unit. The administration mode for the pharmaceutical composition of the invention is not specifically defined; but needless-to-say, the composition is administered as a preparation form suitable to the administration method employed.

Preferred is topical administration (transdermal administration, etc.).

The dose of the therapeutic agent for dyskeratosis including psoriasis vulgaris is preferably determined in consideration of the property and the degree of the disease, the condition of the patient such as the age, the body weight and others thereof, and the administration method. In general, the dose is generally from 0.01to 1000 mg/human/day, preferably from 0.1to 500mg/human/day as the effective amount of the compound of the invention for adults.

As the case may be, a dose lower than the above may be enough, or on the contrary, a dose larger than the above will have to be necessary. The dose may be divided into 2 to 5portions, which may be administered at different times a day.

EXAMPLES

The invention is described in more detail with reference to the following Reference Examples, Examples, Test Examples and Formulation Examples, to which, however, the invention should not be limited.

Reference Example 1

3-(t-butyldimethylsilyloxy)-3-methylbutyric acid

Step 1:

4-Dimethylaminopyridine (0.78g) was added to an anhydrous methylene chloride solution of 3-hydroxy-3-methylbutyric acid (3.76g) and benzyl alcohol (4.13g), and stirred with cooling on ice. N,N'-dicyclohexylcarbodiimide (9.9g) was added thereto, then the ice bath was removed, and stirred overnight at room temperature. The precipitated insoluble matter was removed by filtration, and the mother liquid was concentrated to give a residual oil (13g). This was purified through silica gel column chromatography to give benzyl 3-hydroxy-3-ethylbutyrate (7.2g) as a pale yellow oil.
$^1$H-NMR (CDCl$_3$) δ: 1.28(6H, s), 2.55(2H, s), 5.16(2H, s), 7.36(5H, s)
Step 2:

2,6-Lutidine (3.6g) was added to an anhydrous methylene chloride solution of benzyl 3-hydroxy-3-methylbutyrate (3.5g) obtained in the step 1, and stirred with cooling with ice. t-butyldimethylsilyl trifluoromethanesulfonate (3.9mL) was gradually added dropwise thereto, and stirred for 1hour with cooling on ice and then for 2hours at room temperature. The reaction liquid was diluted with ethyl acetate, then washed with water, aqueous saturated ammonium chloride solution and aqueous saturated sodium chloride solution, then dried over anhydrous magnesium sulfate and concentrated. 4.5g of the residue was purified through silica gel column chromatography to give benzyl 3-(t-butyldimethylsilyloxy)-3-methylbutyrate (2.62g) as a colorless oil.
$^1$H-NMR (CDCl$_3$) δ: 0.07(6H, s), 0.82. (9H, s), 1.36 (6H, s), 2.52(2H, s), 5.09(2H, s), 7.35(5H, s)
Step 3:

Benzyl 3-(t-butyldimethylsilyloxy)-3-methylbutyrate (2.37g) obtained in the step 2was dissolved in ethyl acetate (30mL), and 10% palladium-carbon (0.47g) was added thereto for hydrogenation with H$_2$under atmospheric pressure. After 40. minutes stirring, it was stopped, and the catalyst was removed by filtration. The mother liquor was evaporated away under reduced pressure to give the entitled compound (1.70g) as a colorless oil.

$^1$H-NMR (CDCl$_3$) δ: 0.18(6H, s), 0.89(9H, s), 1.40(6H, s), 2.51(2H, s)

Reference Example 2

(1S,3R,20S)-1,3-bis(t-butyldimethylsilyloxy)-9,10-secopregna-5Z,7E,10(19)-triene-20-ol A tetrahydrofuran solution (500. mL) of (1S,3R,20S)-1,3-bis(t-butyldimethylsilyloxy)-pregna-5,7-dien-20-ol (155 mg) (its production method is, for example, described in Non-Patent Reference 23) was bubbled with argon gas with cooling on ice for 10minutes. Next, a 500-W high-pressure mercury lamp of which the cooling layer was circulated with a filter solution of nickel sulfate-copper sulfate (it is described, for example, in Non-Patent Reference 24) was inserted into the reaction bath and irradiation with light was performed for 5minutes with cooling on ice. The reaction liquid was further irradiated for 2.5minutes, and then transferred into a brown flask and refluxed for 3 hours. The solvent was evaporated away under reduced pressure, and the residue was purified through silica gel column chromatography and preparative thin-layer chromatography to give the entitled compound (30mg) as a colorless oil.
$^1$H-NMR (CDCl$_3$) δ: 0.06(12H, s), 0.54(3H, s), 0.88(18H, s), 1.23(3H, d), 2.45(1H, dd), 2.84(1H, dd), 3.71(2H, m), 4.19(1H, m), 4.38(1H, dd), 4.86(1H, d), 5.18(1H, s), 6.03(1H, d), 6.23(1H, d)

Example 1

(1S,3R,20S)-20-(4-hydroxy-4-methylpentanoyloxy)-9,10-secopregna-5Z,7E,10(19)-triene-1,3-diol Step 1:
2,4,6-Trichlorobenzoyl chloride (13μL) was added to a tetrahydrofuran solution (0.5mL) of 4-triethylsilyloxy-4-methylpentanoic acid (20mg) produced according to the method described in Non-Patent Reference 25and triethylamine (11.2μL), and stirred at room temperature for 30minutes. After the precipitated crystal was removed by filtration, tetrahydrofuran was evaporated away, and the residue was dried under reduced pressure. An anhydrous benzene solution (0.5mL) of (1S,3R,20S)-1,3-bis(t-butyldimethylsilyloxy)-9,10-secopregna-5Z,7E,10(19)-triene-20-ol (30. mg) obtained in Reference Example 2, and 4-dimethylaminopyridine (30mg) were added to the residue in an argon gas atmosphere, and stirred at room temperature for 30minutes. The reaction liquid was diluted with ethyl acetate, then washed with aqueous saturated sodium hydrogencarbonate solution and saturated saline in that order, dried over anhydrous magnesium sulfate, and concentrated under reduced pressure. The residue was purified through silica gel column chromatography to give (1S,3R,20S)-20-(4-triethylsilyloxy-4-methylpentanoyloxy)-1,3-bis(t-butyldimethylsilyloxy)-9,10-secopregna-5Z,7E,10(19)-triene (27mg) as a colorless oil.
$^1$H-NMR (CDCl$_3$) δ: 0.06(12H, s), 0.54(3H, s), 0.57(6H, q), 0.87(18H, s), 0.94(9H, t), 1.20(6H, s), 2.36(2H, t), 2.84 (1H, d), 4.19(1H, m), 4.37(1H, dd), 4.85(1H, d), 4.94(1H, m), 5.17(1H, d), 6.02(1H, d), 6.23(1H, d)
Step 2:
A reagent prepared by adding acetic acid (16μL) to 1 M tetra(n-butyl)ammonium fluoride (0.56mL) was added to an anhydrous tetrahydrofuran solution (1mL) of (1S,3R,20S)-20-(4-triethylsilyloxy-4-methylpentanoyloxy)-1,3-bis(t-butyldimethylsilyloxy)-9,10-secopregna-5Z,7E,10(19)-triene (22mg) obtained in the step 1, under an argon atmosphere, and stirred overnight at room temperature. Cold water was added to the reaction liquid, and then the reaction liquid was subjected to extraction with ethyl acetate. The ethyl acetate layer was washed with saturated saline water, then dried over anhydrous magnesium sulfate, and concentrated under reduced pressure. The residue was purified through silica gel column chromatography and preparative thin-layer chromatography to give the entitled compound (7.1mg) of the invention as a colorless powder.

$^1$H-NMR (CDCl$_3$) δ: 0.55(3H, s), 1.23(6H, s), 1.23(3H, d), 1.80(2H, t), 2.39(2H, t), 2.60(1H, dd), 2.83(1H, m), 4.24(1H, m), 4.43(1H, dd), 4.95(1H, m), 4.99(1H, dd), 5.33(1H, br), 6.02(1H d), 6.37(1H, d)

(+)-FABMS m/z 447[M+H]$^+$

Example 2

(1S,3R,20S)-20-(3-hydroxy-3-methylbutanoyloxy)-9,10-secopregna-5Z,7E,10(19)-triene-1,3-diol Step 1:
According to the same method as in the step 1in Example 1but using 3-(t-butyldimethylsilyloxy)-3-methylbutyric acid (Reference Example 1) in place of 4-triethylsilyloxy-4-methylpentanoic acid, (1S,3R,20S)-20-[3-(t-butyldimethylsilyloxy)-3-methylbutanoyloxy]-1,3-bis(t-butyldimethylsilyloxy)-9,10-secopregna-5Z,7E,10(19)-triene was produced.

$^1$H-NMR (CDCl$_3$) δ: 0.06(12H, s), 0.08(6H, s), 0.53(3H, s), (9H, s), 0.87(18H, s), 1.23(3H, d), 1.40(3H, s), 1.36(3H, s), 2.43(2H, brs), 2.84(1H, d), 4.18(1H, m), 4.36(1H, dd), 4.85(1H, d), 4.91(1H, m), 5.17(1H, d), 6.02(1H, d), 6.23(1H, d)

Step 2:
According to the same method as in the step 2in Example 1but using (1S,3R,20S)-20-[3-(t-butyldimethylsilyloxy)-3-methylbutanoyloxy]-1,3-bis(t-butyldimethylsilyloxy)-9,10-secopregna-5Z,7E,10(19)-triene obtained in the step 1in place of (1S,3R,20S)-20-(4-triethylsilyloxy-4-methylpentanoyloxy)-1,3-bis(t-butyldimethylsilyloxy)-9,10-secopregna-5Z,7E,10(19)-triene, the entitled compound of the invention was produced.

$^1$H-NMR (CDCl$_3$) δ: 0.56(3H, s), 1.26(3H, d), 1.27(6H, s), 2.32(1H, dd), 2.44(2H, s), 2.60(1H, dd), 2.84(1H, m), 3.74(1H, br), 4.24(1H, m), 4.43(1H, dd), 4.99(1H, s), 5.01(1H, m), 5.33(1H, s), 6.03(1H, d), 6.37(1H, d)

ESIMS m/z 455[M+Na]$^+$

Example 3

(1S,3R,20S)-20-(5-hydroxy-5-methylhexanoyloxy)-9,10-secopregna-5Z,7E,10(19)-triene-1,3-diol Step 1:
According to the same method as in the step 1in Example 1but using 5-triethylsilyloxy-5-methylhexanoic acid produced according to the method described in Non-Patent Reference 26in place of 4-triethylsilyloxy-4-methylpentanoic acid, (1S,3R,20S)-20-(5-triethylsilyloxy-5-methylhexanoyloxy)-1,3-bis(t-butyldimethylsilyloxy)-9,10-secopregna-5Z,7E,10(19)-triene was produced.

Step 2:
(1S,3R,20S)-20-(5-triethylsilyloxy-5-methylhexanoyloxy)-1,3-bis(t-butyldimethylsilyloxy)-9,10-secopregna-5Z,7E,10(19)-triene obtained in the above step 1 was processed in the same manner as in the step 2in Example 1to give the entitled compound of the invention.

(+)-ESIMS m/z 483.5[M+Na]$^+$

Example 4

(1S,3R,20S)-20-(4,4,4-trifluoro-3-hydroxy-3-methylbutanoyloxy)-9,10-secopregna-5Z,7E,10(19)-triene-1,3-diol Step 1:
According to the same method as in the step 1in Example 1but using 3-(t-butyldimethylsilyloxy)-4,4,4-trifluoro-3-methylbutyric acid in place of 4-triethylsilyloxy-4-methylpentanoic acid, (1S,3R,20S)-20-[3-(t-butyldimethylsilyloxy)-4,4,4-trifluoro-3-methylbutanoyloxy]-1,3-bis(t-butyldimethylsilyloxy)-9,10-secopregna-5Z,7E,10(19)-triene was produced.

Step 2:
(1S,3R,20S)-20-[3-(t-butyldimethylsilyloxy)-4,4,4-trifluoro-3-methylbutanoyloxy]-1,3-bis(t-butyldimethylsilyloxy)-9,10-secopregna-5Z,7E,10(19)-triene obtained in the above step 1was processed in the same manner as in the step 2in Example 1to give the entitled compound of the invention.

(+)-ESIMS m/z 509.3[M+Na]$^+$

Example 5

(1S,3R,20S)-20-(3-hydroxy-4-methylpentanoyloxy)-9,10-secopregna-5Z,7E,10(19)-triene-1,3-diol Step 1:
According to the same method as in the step 1in Example 1but using 3-(t-butyldimethylsilyloxy)-4-methylpentanoic acid produced according to the method described in Non-Patent Reference 27in place of 4-triethylsilyloxy-4-methylpentanoic acid, (1S,3R,20S)-20-[3-(t-butyldimethylsilyloxy)-4-methylpentanoyloxy]-1,3-bis(t-butyldimethylsilyloxy)-9,10-secopregna-5Z,7E,10(19)-triene was produced.

Step 2:
(1S,3R,20S)-20-[3-(t-butyldimethylsilyloxy)-4-methylpentanoyloxy]-1,3-bis(t-butyldimethylsilyloxy)-9,10-secopregna-5Z,7E,10(19)-triene obtained in the above step 1 was processed in the same manner as in the step 2in Example 1to give the entitled compound of the invention.

(+)-ESIMS m/z 469.4[M+Na]$^+$

Example 6

(1S,3R,20S)-20-(4,4,4-trifluorobutanoyloxy-9,10-secopregna-5Z,7E,10(19)-triene-1,3-diol Step 1:
According to the same method as in the step 1in Example 1but using 4,4,4-trifluorobutyric acid in place of 4-triethylsilyloxy-4-methylpentanoic acid, (1S,3R,20S)-20-(4,4,4-trifluorobutanoyloxy)-1,3-bis(t-butyldimethylsilyloxy)-9,10-secopregna-5Z,7E,10(19)-triene was produced.

Step 2
(1S,3R,20S)-20-(4,4,4-trifluorobutanoyloxy)-1,3-bis(t-butyldimethylsilyloxy)-9,10-secopregna-5Z,7E,10(19)- triene obtained in the above step 1 was processed in the same manner as in the step 2 in Example 1 to give the entitled compound of the invention.

(+)-ESIMS m/z 479.3[M+Na]+

Example 7

(1S,3R,20S)-20-[4,4,4-trifluoro-3-hydroxy-3-(trifluoromethyl)butanoyloxy]-9,10-secopregna-5Z,7E,10(19)-triene-1,3-diol Step 1:
According to the same method as in the step 1 in Example 1 but using 3-(t-butyldimethylsilyloxy)-4,4,4-trifluoro-3-(trifluoromethyl)butyric acid in place of 4-triethylsilyloxy-4-methylpentanoic acid, (1S,3R,20S)-20-[3-(t-butyldimethylsilyloxy)-4,4,4-trifluoro-3-(trifluoromethyl)butanoyloxy-1,3-bis(t-butyldimethylsilyloxy)-9,10-secopregna-5Z,7E,10(19)-triene was produced.

Step 2:
(1S,3R,20S)-20-[3-(t-butyldimethylsilyloxy)-4,4,4-trifluoro-3-(trifluoromethyl)butanoyloxy-1,3-bis(t-butyldimethylsilyloxy)-9,10-secopregna-5Z,7E,10(19)-triene obtained in the above step 1 was processed in the same manner as in the step 2 in Example 1 to give the entitled compound of the invention.

(−)-FABMS m/z 539.2[M−H]−

Example 8

(1S,3R,20S)-20-[(2E)-4-hydroxy-4-methylpent-2-enoyloxy]-9,10-secopregna-5Z,7E,10(19)-triene-1,3-diol Step 1:
According to the same method as in the step 1 in Example 1 but using (2E)-4-triethylsiloxy-4-methylpent-2-enoic acid produced according to the method described in Non-Patent Reference 28 in place of 4-triethylsilyloxy-4-methylpentanoic acid, (1S,3R,20S)-20-[(2E)-4-triethylsilyloxy-4-methylpent-2-enoyloxy]-1,3-bis(t-butyldimethylsilyloxy)-9,10-secopregna-5Z,7E,10(19)-triene was produced.

Step 2:
(1S,3R,20S)-20-[(2E)-4-triethylsilyloxy-4-methylpent-2-enoyloxy]-1,3-bis(t-butyldimethylsilyloxy)-9,10-secopregna-5Z,7E,10(19)-triene obtained in the above step 1 was processed in the same manner as in the step 2 in Example 1 to give the entitled compound of the invention.

(+)-ESIMS m/z 467.3. [M+Na]+

Example 9

(1S,3R,20S)-20-(3-cyclopropyl-3-hydroxy-propanoyloxy)-9,10-secopregna-5Z,7E,10(19)-triene-1,3-diol Step 1:
According to the same method as in the step 1 in Example 1 but using 3-(t-butyldimethylsilyloxy)-3-cyclopropylpropionic acid produced according to the method described in Non-Patent Reference 29 in place of 4-triethylsilyloxy-4-methylpentanoic acid, (1S,3R,20S)-20-[3-(t-butyldimethylsilyloxy)-3-cyclopropylpropanoyloxy]-1,3-bis(t-butyldimethylsilyloxy)-9,10-secopregna-5Z,7E,10(19)-triene was produced.

Step 2:
(1S,3R,20S)-20-[3-(t-butyldimethylsilyloxy)-3-cyclopropylpropanoyloxy]-1,3-bis(t-butyldimethylsilyloxy)-9,10-secopregna-5Z,7E,10(19)-triene obtained in the above step 1 was processed in the same manner as in the step 2 in Example 1 to give the entitled compound of the invention.

(+)-ESIMS m/z 467.3[M+Na]+

Example 10

(1S,3R,20S)-20-[(2E)-4-ethyl-4-hydroxyhex-2-enoyloxy]-9,10-secopregna-5Z,7E,10(19)-triene-1,3-diol Step 1:
According to the same method as in the step 1 in Example 1 but using (2E)-4-(t-butyldimethylsilyloxy)-4-ethylhex-2-enoic acid produced according to the method described in Non-Patent Reference 28 in place of 4-triethylsilyloxy-4-methylpentanoic acid, (1S,3R,20S)-20-[(2E)-4-(t-butyldimethylsilyloxy)-4-ethylhex-2-enoyloxy]-1,3-bis(t-butyldimethylsilyloxy)-9,10-secopregna-5Z,7E,10(19)-triene was produced.

Step 2:
(1S,3R,20S)-20-[(2E)-4-(t-butyldimethylsilyloxy)-4-ethylhex-2-enoyloxy]-1,3-bis(t-butyldimethylsilyloxy)-9,10-secopregna-5Z,7E,10(19)-triene obtained in the above step 1 was processed in the same manner as in the step 2 in Example 1 to give the entitled compound of the invention.

(+)-ESIMS m/z 495.5[M+Na]+

Example 11

(1S,3R,20S)-20-(5-hydroxy-5-methylheptanoyloxy)-9,10-secopregna-5Z,7E,10(19)-triene-1,3-diol Step 1:
According to the same method as in the step 1 in Example 1 but using 5-triethylsilyloxy-5-methylheptanoic acid produced according to the method described in Non-Patent Reference 30 in place of 4-triethylsilyloxy-4-methylpentanoic acid, (1S,3R,20S)-20-(5-triethylsilyloxy-5-methylheptanoyloxy)-1,3-bis(t-butyldimethylsilyloxy)-9,10-secopregna-5Z,7E,10(19)-triene was produced.

Step 2:
(1S,3R,20S)-20-(5-triethylsilyloxy-5-methylheptanoyloxy)-1,3-bis(t-butyldimethylsilyloxy)-9,10-secopregna-5Z,7E,10(19)-triene obtained in the above step 1 was processed in the same manner as in the step 2 in Example 1 to give the entitled compound of the invention.

(+)-ESIMS m/z 475.3[M+Na]+

Example 12

(1S,3R,20S)-20-(3-ethyl-3-hydroxypentanoyloxy)-9,10-secopregna-5Z,7E,10(19)-triene-1,3-diol Step 1:
According to the same method as in the step 1 in Example 1 but using 3-ethyl-3-triethylsilyloxypentanoic acid produced according to the method described in Non-Patent Reference 31 in place of 4-triethylsilyloxy-4-methylpentanoic acid, (1S,3R,20S)-20-(3-ethyl-3-triethylsilyloxypentanoyloxy)-1,3-bis(t-butyldimethylsilyloxy)-9,10-secopregna-5Z,7E,10(19)-triene was produced.

Step 2:
(1S,3R,20S)-20-(3-ethyl-3-triethylsilyloxypentanoyloxy)-1,3-bis(t-butyldimethylsilyloxy)-9,10-secopregna-5Z, 7E,10(19)-triene obtained in the above step 1 was processed in the same manner as in the step 2 in Example 1 to give the entitled compound of the invention.

(+)-ESIMS m/z 483.4[M+Na]$^+$

Example 13

(1S,3R,20S)-20-(4-ethyl-4-hydroxyhexanoyloxy)-9,10-secopregna-5Z,7E,10(19)-triene-1,3-diol Step 1:
According to the same method as in the step 1 in Example 1 but using 4-ethyl-4-triethylsilyloxyhexanoic acid produced according to the method described in Non-Patent Reference 32 in place of 4-triethylsilyloxy-4-methylpentanoic acid, (1S,3R,20S)-20-(4-ethyl-4-triethylsilyloxyhexanoyloxy)-1,3-bis(t-butyldimethylsilyloxy)-9,10-secopregna-5Z,7E,10(19)-triene was produced.

Step 2:
(1S,3R,20S)-20-(4-ethyl-4-triethylsilyloxyhexanoyloxy)-1,3-bis(t-butyldimethylsilyloxy)-9,10-secopregna-5Z,7E,10(19)-triene obtained in the above step 1 was processed in the same manner as in the step 2 in Example 1 to give the entitled compound of the invention.

(+)-ESIMS m/z 497.5[M+Na]$^+$

Example 14

(1S,3R,20S)-20-[3-(1-hydroxy-1-methylethyl)-benzoyloxy]-9,10-secopregna-5Z,7E,10(19)-triene-1,3-diol Step 1:
According to the same method as in the step 1 in Example 1 but using 3-(1-triethylsilyloxy-1-methylethyl)benzoic acid produced according to the method described in Non-Patent Reference 33 in place of 4-triethylsilyloxy-4-methylpentanoic acid, (1S,3R,20S)-20-[3-(1-triethylsilyloxy-1-methylethyl)benzoyloxy]-1,3-bis(t-butyldimethylsilyloxy)-9,10-secopregna-5Z,7E,10(19)-triene was produced.

Step 2:
(1S,3R,20S)-20-[3-(1-triethylsilyloxy-1-methylethyl)benzoyloxy]-1,3-bis(t-butyldimethylsilyloxy)-9,10-secopregna-5Z,7E,10(19)-triene obtained in the above step 1 was processed in the same manner as in the step 2 in Example 1 to give the entitled compound of the invention.

(+)-ESIMS m/z 517.4[M+Na]$^+$

Example 15

(1S,3R,20S)-20-[N-(isopropylsulfonyl)-3-aminopropanoyloxy]-9,10-secopregna-5Z,7E,10(19)-triene-1,3-diol Step 1:
According to the same method as in the step 1. in Example 1 but using N-(isopropylsulfonyl)-β-alanine produced according to the method described in Patent Reference 3 in place of 4-triethylsilyloxy-4-methylpentanoic acid, (1S,3R,20S)-20-[N-(isopropylsulfonyl)-3-aminopropanoyloxy]-1,3-bis(t-butyldimethylsilyloxy)-9,10-secopregna-5Z,7E,10(19)-triene was produced.

Step 2:
(1S,3R,20S)-20-[N-(isopropylsulfonyl)-3-aminopropanoyloxy]-1,3-bis(t-butyldimethylsilyloxy)-9,10-secopregna-5Z,7E,10(19)-triene obtained in the above step 1 was processed in the same manner as in the step 2 in Example 1 to give the entitled compound of the invention.

(+)-ESIMS m/z 532.4[M+Na]$^+$

Example 16

(1S,3R,20S)-20-(6-hydroxy-6-methylheptanoyloxy)-9,10-secopregna-5Z,7E,10(19)-triene-1,3-diol Step 1:
According to the same method as in the step 1 in Example 1 but using 6-triethylsilyloxy-6-methylheptanoic acid produced according to the method described in Non-Patent Reference 35 in place of 4-triethylsilyloxy-4-methylpentanoic acid, (1S,3R,20S)-20-(6-triethylsilyloxy-6-methylheptanoyloxy)-1,3-bis(t-butyldimethylsilyloxy)-9,10-secopregna-5Z,7E,10(19)-triene was produced.

Step 2:
(1S,3R,20S)-20-(6-triethylsilyloxy-6-methylheptanoyloxy)-1,3-bis(t-butyldimethylsilyloxy)-9,10-secopregna-5Z,7E,10(19)-triene obtained in the above step 1 was processed in the same manner as in the step 2 in Example 1 to give the entitled compound of the invention.

(+)-ESIMS m/z 497.4[M+Na]$^+$

Example 17

(1S,3R,20S)-20-{4-[2,2,2-trifluoro-1-hydroxy-1-(trifluoromethyl)ethyl]benzoyloxy}-9,10-secopregna-5Z,7E,10(19)-triene-1,3-diol Step 1:
According to the same method as in the step 1 in Example 1 but using 4-{2,2,2-trifluoro-1-trifluoromethyl-1-[2-(trimethylsilyl)ethoxymethyloxy]ethyl}benzoic acid in place of 4-triethylsilyloxy-4-methylpentanoic acid, (1S,3R,20S)-20-[4-{2,2,2-trifluoro-1-trifluoromethyl-1-[2-(trimethylsilyl)ethoxymethyloxy]ethyl}benzoyloxy]-1,3-bis(t-butyldimethylsilyloxy)-9,10-secopregna-5Z,7E,10(19)-triene was produced.

Step 2:
(1S,3R,20S)-20-[4-{2,2,2-trifluoro-1-trifluoromethyl-1-[2-(trimethylsilyl)ethoxymethyloxy]ethyl}benzoyloxy]-1,3-bis(t-butyldimethylsilyloxy)-9,10-secopregna-5Z,7E,10(19)-triene obtained in the above step 1 was processed in the same manner as in the step 2 in Example 1 to give the entitled compound of the invention.

Example 18

(1S,3R,20S)-20-(5,5,5-trifluoropentanoyloxy)-9,10-secopregna-5Z,7E,10(19)-triene-1,3-diol Step 1:
According to the same method as in the step 1 in Example 1 but using 5,5,5-trifluoropentanoic acid in place of 4-triethylsilyloxy-4-methylpentanoic acid, (1S,3R,20S)-20-(5,5,5-trifluoropentanoyloxy)-1,3-bis(t-butyldimethylsilyloxy)-9,10-secopregna-5Z,7E,10(19)-triene was produced.

Step 2:
(1S,3R,20S)-20-(5,5,5-trifluoropentanoyloxy)-1,3-bis(t-butyldimethylsilyloxy)-9,10-secopregna-5Z,7E,10(19)-triene obtained in the above step 1 was processed in the same manner as in the step 2 in Example 1 to give the entitled compound of the invention.

(+)-ESIMS m/z 493.3[M+Na]$^+$

Example 19

(1S,3R,20S)-20-[N-(2-hydroxy-2-methylpropyl)-N-methyl-2-aminoacetyloxy]-9,10-secopregna-5Z,7E,10(19)-triene-1,3-diol Step 1:
According to the same method as in the step 1 in Example 1 but using N-(2-triethylsilyloxy-2-methylpropyl)-N-methyl-2-aminoacetic acid produced according to the method described in Non-Patent Reference 40 in place of 4-triethylsilyloxy-4-methylpentanoic acid, (1S,3R,20S)-20-[N-(2-triethylsilyloxy-2-methylpropyl)-N-methyl-2-aminoacetyloxy]-1,3-bis(t-butyldimethylsilyloxy)-9,10-secopregna-5Z,7E,10(19)-triene was produced.

Step 2:
(1S,3R,20S)-20-[N-(2-triethylsilyloxy-2-methylpropyl)-N-methyl-2-aminoacetyloxy]-1,3-bis(t-butyldimethylsilyloxy)-9,10-secopregna-5Z,7E,10(19)-triene obtained in the above step 1 was processed in the same manner as in the step 2 in Example 1 to give the entitled compound of the invention.
(+)-ESIMS m/z 476.4[M+1]$^+$

Example 20

(1S,3R,20S)-20-[3-(1-hydroxycyclopentyl)propanoyloxy]-9,10-secopregna-5Z,7E,10(19)-triene-1,3-diol Step 1:
According to the same method as in the step 1 in Example 1 but using 3-(1-triethylsilyloxycyclopentyl)propionic acid produced according to the method described in Non-Patent Reference 36 in place of 4-triethylsilyloxy-4-methylpentanoic acid, (1S,3R,20S)-20-[3-(1-triethylsilyloxycyclopentyl)propanoyloxy]-1,3-bis(t-butyldimethylsilyloxy)-9,10-secopregna-5Z,7E,10(19)-triene was produced.

Step 2:
(1S,3R,20S)-20-[3-(1-triethylsilyloxycyclopentyl)propanoyloxy]-1,3-bis(t-butyldimethylsilyloxy)-9,10-secopregna-5Z,7E,10(19)-triene obtained in the above step 1 was processed in the same manner as in the step 2 in Example 1 to give the entitled compound of the invention.
(+)-ESIMS m/z 473.5[M+1]$^+$

Example 21

(1S,3R,20S)-20-(3,3-difluoro-4-hydroxy-4-methylpentanoyloxy)-9,10-secopregna-5Z,7E,10(19)-triene-1,3-diol Step 1:
According to the same method as in the step 1 in Example 1 but using 4-triethylsilyloxy-3,3-difluoro-4-methylpentanoic acid produced according to the method described in Patent Reference 4 in place of 4-triethylsilyloxy-4-methylpentanoic acid, (1S,3R,20S)-20-(4-triethylsilyloxy-3,3-difluoro-4-methylpentanoyloxy)-1,3-bis(t-butyldimethylsilyloxy)-9,10-secopregna-5Z,7E,10(19)-triene was produced.

Step 2:
(1S,3R,20S)-20-(4-triethylsilyloxy-3,3-difluoro-4-methylpentanoyloxy)-1,3-bis(t-butyldimethylsilyloxy)-9,10-secopregna-5Z,7E,10(19)-triene obtained in the above step 1 was processed in the same manner as in the step 2 in Example 1 to give the entitled compound of the invention.
(+)-ESIMS m/z 483.4[M+1]$^+$

Example 22

(1S,3R,20S)-20-[(3S)-3,4-dihydroxy-4-methylpentanoyloxy]-9,10-secopregna-5Z,7E,10(19)-triene-1,3-diol Step 1:
According to the same method as in the step 1 in Example 1 but using (3S)-3,4-bis(triethylsilyloxy)-4-methylpentanoic acid produced according to the method described in Non-Patent Reference 37 in place of 4-triethylsilyloxy-4-methylpentanoic acid, (1S,3R,20S)-20-[(3S)-3,4-bis(triethylsilyloxy)-4-methylpentanoyloxy]-1,3-bis(t-butyldimethylsilyloxy)-9,10-secopregna-5Z,7E,10(19)-triene was produced.

Step 2:
(1S,3R,20S)-20-[(3S)-3,4-bis(triethylsilyloxy)-4-methylpentanoyloxy]-1,3-bis(t-butyldimethylsilyloxy)-9,10-secopregna-5Z,7E,10(19)-triene obtained in the above step 1 was processed in the same manner as in the step 2 in Example 1 to give the entitled compound of the invention.
(+)-ESIMS m/z 485.4[M+Na]$^+$

Example 23

(1S,3R,20S)-20-(5,5,5-trifluoro-4-hydroxy-4-methylpentanoyloxy)-9,10-secopregna-5Z,7E,10(19)-triene-1,3-diol Step 1:
According to the same method as in the step 1 in Example 1 but using (4-(t-butyldimethylsilyloxy)-5,5,5-trifluoro-4-methylpentanoic acid produced according to the method described in Non-Patent Reference 41 in place of 4-triethylsilyloxy-4-methylpentanoic acid, (1S,3R,20S)-20-[4-(t-butyldimethylsilyloxy)-5,5,5-trifluoro-4-methylpentanoyloxy]-1,3-bis(t-butyldimethylsilyloxy)-9,10-secopregna-5Z,7E,10(19)-triene was produced.

Step 2:
(1S,3R,20S)-20-[4-(t-butyldimethylsilyloxy)-5,5,5-trifluoro-4-methylpentanoyloxy]-1,3-bis(t-butyldimethylsilyloxy)-9,10-secopregna-5Z,7E,10(19)-triene obtained in the above step 1 was processed in the same manner as in the step 2 in Example 1 to give the entitled compound of the invention.
(+)-ESIMS m/z 523.3[M+Na]$^+$

Example 24

(1S,3R,20R)-20-(4-hydroxy-4-methylpentanoyloxy)-9,10-secopregna-5Z,7E,10(19)-triene-1,3-diol Step 1:
According to the same method as in the step 1 in Example 1 but using (1S,3R,20R)-1,3-bis(t-butyldimethylsilyloxy)-9,10-secopregna-5Z,7E,10(19)-trien-20-ol produced according to the method described in Non-Patent Reference 16 in place of (1S,3R,20S)-1,3-bis(t-butyldimethylsilyloxy)-9,10-secopregna-5Z,7E,10(19)-trien-20-ol, (1S,3R,20R)-20-(4-triethylsilyloxy-4-methylpentanoyloxy)-1,3-bis(t-butyldimethylsilyloxy)-9,10-secopregna-5Z,7E,10(19)-triene was produced.

Step 2:
(1S,3R,20R)-20-(4-triethylsilyloxy-4-methylpentanoyloxy)-1,3-bis(t-butyldimethylsilyloxy)-9,10-secopregna-5Z,7E,10(19)-triene obtained in the above step 1 was processed in the same manner as in the step 2 in Example 1 to give the entitled compound of the invention.

(+)-ESIMS m/z 469.4[M+Na]$^+$

Example 25

(1S,3R,20R)-20-(3-hydroxy-3-methylbutanoyloxy)-9,10-secopregna-5Z,7E,10(19)-triene-1,3-diol Step 1:

According to the same method as in the step 1 in Example 2 but using (1S,3R,20R)-1,3-bis(t-butyldimethylsilyloxy)-9,10-secopregna-5Z,7E,10(19)-trien-20-ol produced according to the method described in Non-Patent Reference 16 in place of (1S,3R,20S)-1,3-bis(t-butyldimethylsilyloxy)-9,10-secopregna-5Z,7E,10(19)-trien-20-ol, (1S,3R,20R)-20-(3-t-butyldimethylsilyloxy-3-methylbutanoyloxy)-1,3-bis(t-butyldimethylsilyloxy)-9,10-secopregna-5Z,7E,10(19)-triene was produced.

Step 2:

(1S,3R,20R)-20-(3-t-butyldimethylsilyloxy-3-methylbutanoyloxy)-1,3-bis(t-butyldimethylsilyloxy)-9,10-secopregna-5Z,7E,10(19)-triene obtained in the above step 1 was processed in the same manner as in the step 2 in Example 1 to give the entitled compound of the invention.

(+)-FABMS m/z 432[M+1]$^+$

Example 26

(1S,3R,17β)-17-(4-hydroxy-4-methylpentanoyloxymethyl)-9,10-secoandrosta-5Z,7E,10(19)-triene-1,3-diol Step 1:

According to the same method as in the step 1 in Example 1 but using (1S,3R,17β)-1,3-bis(t-butyldimethylsilyloxy)-17-hydroxymethyl-9,10-secoandrosta-5Z,7E,10(19)-triene produced according to the method described in Non-Patent Reference 17 in place of (1S,3R,20S)-1,3-bis(t-butyldimethylsilyloxy)-9,10-secopregna-5Z,7E,10(19)-trien-20-ol, (1S,3R,17β)-17-(4-triethylsilyloxy-4-methylpentanoyloxymethyl)-1,3-bis(t-butyldimethylsilyloxy)-9,10-secoandrosta-5Z,7E,10(19)-triene was produced.

Step 2:

(1S,3R,17β)-17-(4-triethylsilyloxy-4-methylpentanoyloxymethyl)-1,3-bis(t-butyldimethylsilyloxy)-9,10-secoandrosta-5Z,7E,10(19)-triene obtained in the above step 1 was processed in the same manner as in the step 2 in Example 1 to give the entitled compound of the invention.

(+)-ESIMS m/z 455.3[M+Na]$^+$

Example 27

(1S,3R,20S)-20-(4-hydroxy-4-methyl-3-oxo-pentanoyloxy)-9,10-secopregna-5Z,7E,10(19)-triene-1,3-diol Step 1:

According to the same method as in the step 1 in Example 1 but using 4-(t-butyldimethylsilyloxy)-4-methylpent-2-ynoic acid produced according to the method described in Non-Patent Reference 38 in place of 4-triethylsilyloxy-4-methylpentanoic acid, (1S,3R,20S)-20-[4-(t-butyldimethylsilyloxy)-4-methylpent-2-ynoyloxy]-1,3-bis(t-butyldimethylsilyloxy)-9,10-secopregna-5Z,7E,10(19)-triene was produced.

Step 2:

A reagent prepared by adding acetic acid (14μL) to 1 M tetra-n-butylammonium fluoride (0.81ml) was added to an anhydrous tetrahydrofuran solution (0.4mL) of (1S,3R,20S)-20-[4-(t-butyldimethylsilyloxy)-4-methylpent-2-ynoyloxy]-1,3-bis(t-butyldimethylsilyloxy)-9,10-secopregna-5Z,7E,10(19)-triene (32mg) obtained in the step 1, in an argon atmosphere, and stirred overnight at room temperature. Water was added to the reaction liquid, and then the reaction liquid was subjected to extraction three times with chloroform. The chloroform layer was then washed with saturated saline, dried over anhydrous magnesium sulfate, and concentrated under reduced pressure. The residue was purified through silica gel column chromatography to give the entitled compound (9.5mg) of the invention as a pale brown powder.

(+)-ESIMS m/z 483.3[M+Na]$^+$

Example 28

(1S,3R,20S)-20-(4-ethyl-4-hydroxy-3-oxo-hexanoyloxy)-9,10-secopregna-5Z,7E,10(19)-triene-1,3-diol Step 1:

According to the same method as in the step 1 in Example 1 but using 4-triethylsilyloxy-4-ethylhex-2-ynic acid produced according to the method described in Non-Patent Reference 38 in place of 4-triethylsilyloxy-4-methylpentanoic acid, (1S,3R,20S)-20-[4-(t-butyldimethylsilyloxy)-4-ethylhex-2-ynoyloxy]-1,3-bis(t-butyldimethylsilyloxy)-9,10-secopregna-5Z,7E,10(19)-triene was produced.

Step 2:

(1S,3R,20S)-20-[4-(t-butyldimethylsilyloxy)-4-ethylhex-2-ynoyloxy]-1,3-bis(t-butyldimethylsilyloxy)-9,10-secopregna-5Z,7E,10(19)-triene obtained in the above step 1 was processed in the same manner as in the step 2 in Example 27 to give the entitled compound of the invention.

(+)-ESIMS m/z 511.5[M+Na]$^+$

Example 29

(1S,3R,20S)-20-[3-(hydroxymethyl)phenylacetyloxy]-9,10-secopregna-5Z,7E,10(19)-triene-1,3-diol Step 1:

According to the same method as in the step 1 in Example 1 but using 3-(t-butyldimethylsilyloxymethyl)phenylacetic acid produced according to the method described in Non-Patent Reference 42 in place of 4-triethylsilyloxy-4-methylpentanoic acid, (1S,3R,20S)-20-[3-(t-butyldimethylsilyloxymethyl)phenylacetyloxy]-1,3-bis(t-butyldimethylsilyloxy)-9,10-secopregna-5Z,7E,10(19)-triene was produced.

Step 2:

(1S,3R,20S)-20-[3-(t-butyldimethylsilyloxymethyl)phenylacetyloxy]-1,3-bis(t-butyldimethylsilyloxy)-9,10-secopregna-5Z,7E,10(19)-triene obtained in the above step 1 was

Example 30

(1S,3R,17β)-17-[(2E)-4-ethyl-4-hydroxy-hex-2-enoyloxymethyl]-9,10-secoandrosta-5Z,7E,10(19)-triene-1,3-diol Step 1:
According to the same method as in the step 1 in Example 10 but using (1R,3R,17β)-1,3-bis(t-butyldimethylsilyloxy)-17-hydroxymethyl-9,10-secoandrosta-5Z,7E,10(19)-triene produced according to the method described in Non-Patent Reference 17 in place of (1S,3R,20S)-1,3-bis(t-butyldimethylsilyloxy)-9,10-secoprena-5Z,7Z,10(19)-trien-2-ol, (1S,3R,17β)-17-[(2E)-4-(t-butyldimethylsilyloxy)-4-ethylhex-2-enoyloxymethyl]-1,3-bis(t-butyldimethylsilyloxy)-9,10-secoandrosta-5Z,7E,10(19)-triene was produced.

Step 2:
(1S,3R,17β)-17-[(2E)-4-(t-butyldimethylsilyloxy)-4-ethylhex-2-enoyloxymethyl]-1,3-bis(t-butyldimethylsilyloxy)-9,10-secoandrosta-5Z,7E,10(19)-triene obtained in the above step 1 was processed in the same manner as in the step 2 in Example 1 to give the entitled compound of the invention.

(+)-ESIMS m/z 481.4[M+Na]$^+$

Example 31

(1S,3R,20S)-20-[(3R)-3,4-dihydroxy-4-methylpentanoyloxy]-9,10-secopregna-5Z,7E,10(19)-triene-1,3-diol Step 1:
According to the same method as in the step 1 in Example 1 but using (3R)-3,4-bis(triethylsilyloxy)-4-methylpentanoic acid produced according to the method described in Non-Patent Reference 37 in place of 4-triethylsilyloxy-4-methylpentanoic acid, (1S,3R,20S)-20-[(3R)-3,4-bis(triethylsilyloxy)-4-methylpentanoyloxy]-1,3-bis(t-butyldimethylsilyloxy)-9,10-secopregna-5Z,7E,10(19)-triene was produced.

Step 2:
(1S,3R,20S)-20-[(3R)-3,4-bis(triethylsilyloxy)-4-methylpentanoyloxy]-1,3-bis(t-butyldimethylsilyloxy)-9,10-secopregna-5Z,7E,10(19)-triene obtained in the above step 1 was processed in the same manner as in the step 2 in Example 1 to give the entitled compound of the invention.

(+)-ESIMS m/z 485.4[M+Na]$^+$

Example 32

(1S,3R,20S)-20-[5,5,5-trifluoro-4-hydroxy-4-(trifluoromethyl)pentanoyloxy]-9,10-secopregna-5Z,7E,10(19)-triene-1,3-diol Step 1:
According to the same method as in the step 1 in Example 1 but using 4-(t-butyldimethylsilyloxy)-5,5,5-trifluoro-4-(trifluoromethyl)pentanoic acid produced according to the method described in Non-Patent Reference 41 in place of 4-triethylsilyloxy-4-methylpentanoic acid, (1S,3R,20S)-20-[4-(t-butyldimethylsilyloxy)-5,5,5-trifluoro-4-(trifluoromethyl)pentanoyloxy]-1,3-bis(t-butyldimethylsilyloxy)-9,10-secopregna-5Z,7E,10(19)-triene was produced.

Step 2:
(1S,3R,20S)-20-[4-(t-butyldimethylsilyloxy)-5,5,5-trifluoro-4-(trifluoromethyl)pentanoyloxy]-1,3-bis(t-butyldimethylsilyloxy)-9,10-secopregna-5Z,7E,10(19)-triene obtained in the above step 1 was processed in the same manner as in the step 2 in Example 1 to give the entitled compound of the invention.

(+)-ESIMS m/z 577.3[M+Na]$^+$

Example 33

(1S,3R,20S)-20-(3-hydroxy-3-n-propylhexanoyloxy)-9,10-secopregna-5Z,7E,10(19)-triene-1,3-diol Step 1:
According to the same method as in the step 1 in Example 1 but using 3-hydroxy-3-n-propylhexanoic acid produced according to the method described in Non-Patent Reference 44 in place of 4-triethylsilyloxy-4-methylpentanoic acid, (1S,3R,20S)-20-(3-hydroxy-3-n-propylhexanoyloxy)-1,3-bis(t-butyldimethylsilyloxy)-9,10-secopregna-5Z,7E,10(19)-triene was produced.

Step 2:
(1S,3R,20S)-20-(3-hydroxy-3-n-propylhexanoyloxy)-1,3-bis(t-butyldimethylsilyloxy)-9,10-secopregna-5Z,7E,10(19)-triene obtained in the above step 1 was processed in the same manner as in the step 2 in Example 1 to give the entitled compound of the invention.

(+)-ESIMS m/z 511.5[M+Na]$^+$

Example 34

(1S,3R,20S)-20-(5-hydroxy-5-ethylheptanoyloxy)-9,10-secopregna-5Z,7E,10(19)-triene-1,3-diol Step 1:
2,4,6-Trichlorobenzoyl chloride (22μL) was added to a tetrahydrofuran solution (0.5mL) of 5-triethylsilyloxy-5-ethylheptanoic acid (40mg) produced according to the method described in Non-Patent Reference 45 and triethylamine (20μL), and stirred at room temperature for 15 hours. After the precipitated crystal was collected by filtration, tetrahydrofuran was evaporated away, and the residue was dried under reduced pressure. To the residue, added were an anhydrous toluene solution (1mL) of (1S,3R,20S)-1,3-bis(t-butyldimethylsilyloxy)-9,10-secopregna-5Z,7E,10(19)-trien-2-ol (26mg), and 4-dimethylaminopyridine (51mg), in an argon atmosphere, and stirred at room temperature for 30 minutes. The reaction liquid was diluted with ethyl acetate, washed with aqueous saturated sodium hydrogencarbonate solution and saturated saline in that order, dried over anhydrous magnesium sulfate, and concentrated under reduced pressure. The residue was purified through silica gel column chromatography to give (1S,3R,20S)-20-(5-triethylsilyloxy-5-ethylheptanoyloxy)-1,3-bis(t-butyldimethylsilyloxy)-9,10-secopregna-5Z,7E,10(19)-triene (39mg) as a colorless powder.

Step 2:
A reagent prepared by adding acetic acid (19μL) to 1 M tetra(n-butyl)ammonium fluoride (0.94mL) was added to an anhydrous tetrahydrofuran solution (1mL) of (1S,3R,20S)-20-(5-triethylsilyloxy-5-ethylheptanoyloxy)-1,3-bis(t-butyldimethylsilyloxy)-9,10-secopregna-5Z,7E,10(19)-triene (39mg) obtained in the step 1, in an argon atmosphere, and stirred overnight at room temperature. Cold water was added to the reaction liquid, and then the liquid was subjected to extraction with ethyl acetate. The ethyl acetate layer was washed with saturated saline, then dried over anhydrous magnesium sulfate, and concentrated under reduced pressure. The residue was purified through silica gel column chromatography and partitioning thin-layer chromatography to give the entitled compound (7.1mg) of the invention as a colorless powder.

(+)-ESIMS m/z 511.5[M+Na]+

Example 35

(1S,3R,20S)-20-[(4R) or (4S)-5,5,5-trifluoro-4-hydroxy-4-methylpentanoyloxy]-9,10-secopregna-5Z,7E,10(19)-triene-1,3-diol Step 1:
According to the same method as in the step 1in Example 34but using 4-(t-butyldimethylsilyloxy)-5,5,5-trifluoro-4-methylpentanoic acid produced according to the method described in Non-Patent Reference 41in place of 5-triethylsilyloxy-5-ethylheptanoic acid, (1S,3R,20S)-20-[4-(t-butyldimethylsilyloxy)-5,5,5-trifluoro-4-methylpentanoyloxy]-1,3-bis(t-butyldimethylsilyloxy)-9,10-secopregna-5Z,7E,10(19)-triene was produced.
Step 2:
(1S,3R,20S)-20-[4-(t-butyldimethylsilyloxy)-5,5,5-trifluoro-4-methylpentanoyloxy]-1,3-bis(t-butyldimethylsilyloxy)-9,10-secopregna-5Z,7E,10(19)-triene obtained in the above step 1was processed in the same manner as in the step 2in Example 1, and the product was purified by high-performance liquid chromatography [DAICEL CHIRALPAK AD-RH (4.6×150mm ID), 55% acetonitrile-water, 0.5ml/min, 40° C., UV 254nm]. The solution containing the compound that had been eluted first was concentrated to give the entitled compound of the invention.
$^1$H-NMR (CDCl$_3$) δ: 0.55(3H, s), 1.25(3H, d, J=6.2. Hz), 1.338(3H, s), 2.51(2H, t, J=7.2Hz), 2.85(1H, m), 4.24 (1H, m), 4.44(1H, m), 4.98(1H, m), 4.99(1H, brs), 5.33 (1H, brs), 6.03(1H, d, J=11.4Hz), 6.37(1H, d, J=11.4Hz)

Example 36

(1S,3R,20S)-20-[(4S) or (4R)-5,5,5-trifluoro-4-hydroxy-4-methylpentanoyloxy]-9,10-secopregna-5Z,7E,10(19)-triene-1,3-diol In the fractionation step in high-performance liquid chromatography in Example 35, the solution containing the compound that had been eluted later was concentrated and purified to give the entitled compound of the invention.
$^1$H-NMR (CDCl$_3$) δ: 0.55(3H, s), 1.25(3H, d, J=6.2Hz), 1.333(3H, s), 2.51(2H, t, J=7.2Hz), 2.85(1H, m), 4.24 (1H, m), 4.44(1H, m), 4.98(1H, m), 4.99(1H, brs), 5.33 (1H, brs), 6.03(1H, d, J=11.4Hz), 6.37(1H, d, J=11.4Hz)

Example 37

(1S,3R,20S)-20-(6,6,6-trifluoro-5-hydroxy-5-methylhexanoyloxy)-9,10-secopregna-5Z,7E,10(19)-triene-1,3-diol Step 1:
According to the same method as in the step 1in Example 34but using 5-triethylsilyloxy-6,6,6-trifluoro-5-methylhexanoic acid produced according to the method described in Non-Patent Reference 46in place of 5-triethylsilyloxy-5-ethylheptanoic acid, (1S,3R,20S)-20-(5-triethylsilyloxy-6,6,6-trifluoro-4-methylhexanoyloxy)-1,3-bis(t-butyldimethylsilyloxy)-9,10-secopregna-5Z,7E,10(19)-triene was produced.

Step 2:
(1S,3R,20S)-20-(5-triethylsilyloxy-6,6,6-trifluoro-4-methylhexanoyloxy)-1,3-bis(t-butyldimethylsilyloxy)-9,10-secopregna-5Z,7E,10(19)-triene obtained in the above step 1 was processed in the same manner as in the step 2in Example 34to give the entitled compound of the invention.
(+)-ESIMS m/z 537.4[M+Na]+

Example 38

(1S,3R,20S)-20-(5,5,5-trifluoro-4-hydroxy-4-methyl-3-oxopentanoyloxy)-9,10-secopregna-5Z,7E,10(19)-triene-1,3-diol Step 1:
According to the same method as in the step 1in Example 34but using 4-triethylsilyloxy-5,5,5-trifluoro-4-methylpent-2-ynic acid produced according to the method described in Non-Patent Reference 38in place of 5-triethylsilyloxy-5-ethylheptanoic acid, (1S,3R,20S)-20-(4-triethylsilyloxy-5,5,5-trifluoro-4-methylpent-2-ynoyloxy)-1,3-bis(t-butyldimethylsilyloxy)-9,10-secopregna-5Z,7E,10(19)-triene was produced.
Step 2:
A reagent prepared by adding acetic acid (44.2μL) to 1. M tetra(n-butyl)ammonium fluoride (2.6mL) was added to (1S, 3R,20S)-20-(4-triethylsilyloxy-5,5,5-trifluoro-4-methylpent-2-ynoyloxy)-1,3-bis(t-butyldimethylsilyloxy)-9,10-secopregna-5Z,7E,10(19)-triene (108mg) obtained in the step 1, in an argon atmosphere, and stirred for 23 hours at room temperature. Further, a reagent prepared by adding acetic acid (22μL) to 1M tetra(n-butyl)ammonium fluoride (1.25mL) was added thereto, and stirred at room temperature for 8.5hours. After the reaction liquid was cooled in an ice bath, water was added thereto. The reaction liquid was subjected to extraction three times with chloroform. The chloroform layer was washed with aqueous 1M citric acid solution and saturated saline, then dried over anhydrous magnesium sulfate, and concentrated under reduced pressure. The residue was purified through silica gel column chromatography to give the entitled compound (29mg) of the invention as a white powder.
(+)-ESIMS m/z 537.3[M+Na]+

Example 39

(1S,3R,20S)-20-(4-hydroxy-4-methylpentanoyloxy)-9,10-secopregna-5Z,7E,10(19),16-tetraene-1,3-diol Step 1:
According to the same method as in the step 1in Example 34but using 4-triethylsilyloxy-4-methylpentanoic acid (its production method is, for example, described in Non-Patent Reference 25) in place of 5-triethylsilyloxy-5-ethylheptanoic acid, and using (1S,3R,20S)-1,3-bis(triethylsilyloxy)-20-hydroxypregna-5,7,16-triene produced according to the method described in Patent Reference 6in place of (1S,3R,20S)-1,3-bis(t-butyldimethylsilyloxy)-9,10-secopregna-5Z,7E,10(19)-trien-20-ol, (1S,3R,20S)-bis(triethylsilyloxy)-20-(4-triethylsilyloxy-4-methylpentanoyloxy)-pregna-5,7,16-triene was produced.
Step 2:
(1S,3R,20S)-1,3-bis(triethylsilyloxy)-20-(4-triethylsilyloxy-4-methylpentanoyloxy)-pregna-5,7,16-triene obtained in the above step 1was processed in the same manner as in the step 2 in Example 34 to give (1S,3R,20S)-1,3-bis(triethylsilyloxy)-20-(4-hydroxy-4-methylpentanoyloxy)-pregna-5,7,16-triene.

Step 3:
(1S,3R,20S)-1,3-bis(triethylsilyloxy)-20-(4-hydroxy-4-methylpentanoyloxy)-pregna-5,7,16-triene obtained in the above step 2 was processed in the same manner as in Reference 2 to give the entitled compound of the invention.
(+)-ESIMS m/z 467.3[M+Na]$^+$ Example 40

(1R,3R,20S)-19-nor-20-(4-hydroxy-4-methylpentanoyloxy)-9,10-secopregna-5Z,7E-diene-1,3-diol Step 1:
According to the same method as in the step 1. in Example 34 but using 4-triethylsilyloxy-4-methylpentanoic acid (its production method is, for example, described in Non-Patent Reference 25) in place of 5-triethylsilyloxy-5-ethylheptanoic acid, and using (20S)-des-A,B-8β-triethylsilyloxypregnan-3-ol produced according to the method described in Patent Reference 47 in place of (1S,3R,20S)-1,3-bis(t-butyldimethylsilyloxy)-9,10-secopregna-5Z,7E,10(19)-trien-20-ol, (20S)-des-A,B-8β-triethylsilyloxy-20-(4-triethylsilyloxy-4-methylpentanoyloxy)pregnane was produced.

Step 2:
(20S)-des-A,B-8β-triethylsilyloxy-20-(4-triethylsilyloxy-4-methylpentanoyloxy)pregnane obtained in the above step 1 was processed in the same manner as in the step 2 in Example 34 to give (20S)-des-A,B-20-(4-hydroxy-4-methylpentanoyloxy)pregnan-8β-ol.

Step 3:
In an argon atmosphere, dichloromethane (2mL) was added to (20S)-des-A,B-20-(4-hydroxy-4-methylpentanoyloxy)pregnan-8β-ol (42mg) obtained in the above step 2, 4-methylmorpholine N-oxide (39mg) and 4-angstrom molecular sieves (10mg), and further tetra-N-propylammonium perruthenate (24mg) was added and stirred for 25 minutes. The reaction solution was purified through silica gel column chromatography to give (20S)-des-A,B-20-(4-hydroxy-4-methylpentanoyloxy)pregna-8-one (35mg) as a colorless oil.

Step 4:
In an argon atmosphere, triethylamine (89.8μL) and 4-dimethylaminopyridine (8mg) were added to a dichloromethane solution (0.3ml) of (20S)-des-A,B-20-(4-hydroxy-4-methylpentanoyloxy)pregna-8-one (100mg) obtained in the above step 3, and after being cooled in an ice bath, chlorotriethylsilane (81μL) was added thereto, and stirred at room temperature for 20 hours. After cooling with an ice bath, ether and water were added thereto, and the solution was subjected to extraction three times with ether. The extract was dried over anhydrous magnesium sulfate, and then concentrated under reduced pressure. The residue was purified through silica gel column chromatography to give (20S)-des-A,B-20-(4-triethylsilyloxy-4-methylpentanoyloxy)pregna-8-one (119mg) as a colorless oil.
(+)-ESIMS m/z 425.4[M+1]$^+$, 447.4[M+Na]$^+$ Step 5:
In an argon atmosphere, an anhydrous tetrahydrofuran solution (1.5mL) of {2-[(3'R,5'R)-3',5'-bis(t-butyldimethylsilyloxy)-cyclohexylidene]ethyl}diphenylphosphine oxide (its production method is, for example, described in Non-Patent Reference 48) was cooled in an ice bath, then a hexane solution of n-butyllithium (1.58M, 0.06mL) was dropwise added, and stirred for 30 minutes. Then, after cooling to −78° C., an anhydrous tetrahydrofuran solution (0.3mL) of (20S)-des-A,B-20-(4-triethylsilyloxy-4-methylpentanoyloxy)pregnan-8-one (25mg) obtained in the step 4 was added, and stirred for 3 hours. After warming up to 0° C., the solution was stirred further for 19.5 hours. Aqueous saturated ammonium chloride solution was added thereto, and this was subjected to extraction three times with ethyl acetate. The extract was washed with saturated saline, dried over anhydrous magnesium sulfate, and concentrated under reduced pressure. The residue was purified through silica gel column chromatography to give (1R,3R,20S)-19-nor-1,3-bis(t-butyldimethylsilyloxy)-20-(4-triethylsilyloxy-4-methylpentanoyloxy)-9,10-secopregna-5Z,7E-diene (15mg) as a colorless oil.

Step 6:
(1R,3R,20S)-19-nor-1,3-bis(t-butyldimethylsilyloxy)-20-(4-triethylsilyloxy-4-methylpentanoyloxy)-9,10-secopregna-5Z,7E-diene obtained in the above step 5 was processed in the same manner as in the step 2 in Example 34 to give the entitled compound of the invention.
(+)-ESIMS m/z 457.4[M+Na]$^+$ Example 41

(1R,3R,20S)-2-methylene-19-nor-20-(4-hydroxy-4-methylpentanoyloxy)-9,10-secopregna-5Z,7E-diene-1,3-diol Step 1:
According to the same method as in the step 5 in Example 40 but using {2-[(3'R,5'R)-3',5'-bis(t-butyldimethylsilyloxy)-4'-methylenecyclohexylidene]ethyl}diphenylphosphine oxide (its production method is, for example, described in Non-Patent Reference 49) in place of {2-[(3'R,5'R)-3',5'-bis(t-butyldimethylsilyloxy)-cyclohexylidene]ethyl}diphenylphosphine oxide, (1R,3R,20S)-2-methylene-19-nor-1,3-bis(t-butyldimethylsilyloxy)-20-(4-triethylsilyloxy-4-methylpentanoyloxy)-9,10-secopregna-5Z,7E-diene was produced.

Step 2:
(1R,3R,20S)-2-methylene-19-nor-1,3-bis(t-butyldimethylsilyloxy)-20-(4-triethylsilyloxy-4-methylpentanoyloxy)-9,10-secopregna-5Z,7E-diene obtained in the above step 1 was processed in the same manner as in the step 2 in Example 34 to give the entitled compound of the invention.
(+)-ESIMS m/z 469.5[M+Na]$^+$ Example 42

(1R,3R,20S)-19-nor-20-[(2E)-4-ethyl-4-hydroxyhex-2-enoyloxy]-9,10-secopregna-5Z,7E-diene-1,3-diol Step 1:
Pyridine (0.28mL) and dichloromethane (1mL) were added to (20S)-des-A,B-8β-triethylsilyloxypregnan-20-ol (361mg) produced according to the method described in Patent Reference 47.. After cooling in an ice bath, acetic anhydride (0.22mL) was added thereto, and stirred at room temperature for 21 hours. Further, pyridine (0.14mL) and acetic anhydride (0.11mL) were added, and stirred for 18 hours. The reaction liquid was concentrated under reduced pressure, and the residue was purified through silica gel column chromatography to give (20S)-des-A,B-8β-triethylsilyloxy-20-acetoxypregnane (336mg) as a colorless oil.

Step 2:
A tetrahydrofuran solution of tetra(n-butyl)ammonium (1M, 9.42mL) was added to (20S)-des-A,B-8β-triethylsilyloxy-20-acetoxypregnane (334mg) obtained in the above step 1, with cooling in an ice bath, under stirring at room temperature for 22 hours, then cooled in an ice bath. Water and ether were added thereto, And this was subjected to extraction three times with ether. The extract was washed with aqueous 1M citric acid solution and aqueous saturated sodium chloride solution, dried over anhydrous magnesium sulfate, and concentrated under reduced pressure. The residue was purified through silica gel column chromatography to give (20S)-des-A,B-20-acetoxypregnan-8β-ol (230 mg) as a colorless oil.

Step 3:

According to the same method as in the step 3 in Example 40 but using (20S)-des-A,B-20-acetoxypregnan-8β-ol obtained in the above step 2 in place of (20S)-des-A,B-20-(4-hydroxy-4-methylpentanoyloxy)pregnan-8β-ol, (20S)-des-A,B-20-acetoxypregnan-8-one was produced.

Step 4:

According to the same method as in the step 5 in Example 40 but using (20S)-des-A,B-20-acetoxypregnan-8-one obtained in the above step 3 in place of (20S)-des-A,B-20-(4-triethylsilyloxy-4-methylpentanoyloxy)pregnan-8-one, (1R,3R,20S)-19-nor-1,3-bis(t-butyldimethylsilyloxy)-20-acetoxy-9,10-secopregna-5Z,7E-diene was produced.

Step 5:

A tetrahydrofuran (1 mL)-methanol (1 mL) solution of (1R,3R,20S)-19-nor-1,3-bis(t-butyldimethylsilyloxy)-20-acetoxy-9,10-secopregna-5Z,7E-diene (120 mg) obtained in the above step 4 was cooled in an ice bath. Aqueous 10% potassium hydroxide solution (0.5 mL) was added thereto and stirred at room temperature for 14.5 hours. Aqueous 10% potassium hydroxide solution (0.25 mL) was further added, and stirred for 4.5 hours. Aqueous 10% potassium hydroxide solution (0.25 mL) was further added, and stirred for 20 hours. Tetrahydrofuran and methanol were removed through concentration under reduced pressure. Then water was added to this, and water solution was subjected to extraction three times with ethyl acetate. After washed with aqueous saturated sodium chloride solution, this was dried over anhydrous magnesium sulfate, and concentrated under reduced pressure. The residue was purified through silica gel column chromatography to give (1R,3R,20S)-19-nor-1,3-bis(t-butyldimethylsilyloxy)-9,10-secopregna-5Z,7E-dien-20-ol (94 mg) as a white powder.

Step 6:

According to the same method as in the step 1 in Example 34 but using (2E)-4-triethylsilyloxy-4-ethylhex-2-enoic acid produced according to the method described in Non-Patent Reference 28 in place of 5-triethylsilyloxy-5-ethylheptanoic acid and using (1R,3R,20S)-19-nor-1,3-bis(t-butyldimethylsilyloxy)-9,10-secopregna-5Z,7E-dien-20-ol obtained in the above step 5 in place of (1R,3R,20S)-1,3-bis(t-butyldimethylsilyloxy)-9,10-secopregna-5Z,7E,10(19)-trien-20-ol, (1R,3R,20S)-19-nor-1,3-bis(t-butyldimethylsilyloxy)-20[[(2E)-4-ethyl-4-triethylsilyloxyhex-2-enoyloxy]-9,10-secopregna-5Z,7E-diene was produced.

Step 7:

(1R,3R,20S)-19-nor-1,3-bis(t-butyldimethylsilyloxy)-20[[(2E)-4-ethyl-4-triethylsilyloxyhex-2-enoyloxy]-9,10-secopregna-5Z,7E-diene obtained in the above step 6 was processed in the same manner as in the step 2 in Example 34 to give the entitled compound of the invention.

(+)-ESIMS m/z 483.4[M+Na]$^+$

Example 43

(1R,3R,20S)-19-nor-20-(5,5,5-trifluoro-4-hydroxy-4-methylpentanoyloxy)-9,10-secopregna-5Z,7E-diene-1,3-diol Step 1:

According to the same method as in the step 6 in Example 42 but using 4-triethylsilyloxy-5,5,5-trifluoro-4-methylpentanoic acid produced according to the method described in Non-Patent Reference 41 in place of (2E)-4-triethylsilyloxy-4-ethylhex-2-enoic acid, (1R,3R,20S)-19-nor-1,3-bis(t-butyldimethylsilyloxy)-20-(4-triethylsiloxy-5,5,5-trifluoro-4-methylpentanoyloxy)-9,10-secopregna-5Z,7E-diene was produced.

Step 2:

(1R,3R,20S)-19-nor-1,3-bis(t-butyldimethylsilyloxy)-20-(4-triethylsiloxy-5,5,5-trifluoro-4-methylpentanoyloxy)-9,10-secopregna-5Z,7E-diene obtained in the above step 1 was processed in the same manner as in the step 2 in Example 34 to give the entitled compound of the invention.

(+)-ESIMS m/z 511.4[M+Na]$^+$

Example 44

(1R,3R,20S)-2-methylene-19-nor-20-(5,5,5-trifluoro-4-hydroxy-4-methylpentanoyloxy)-9,10-secopregna-5Z,7E-diene-1,3-diol Step 1:

According to the same method as in the step 4 in Example 42 but using {2-[(3'R,5'R)-3',5'-bis(t-butyldimethylsilyloxy)-4'-methylenecyclohexylidene]ethyl}diphenylphosphine oxide (its production method is, for example, described in Non-Patent Reference 49) in place of {2-[(3'R,5'R)-3',5'-bis(t-butyldimethylsilyloxy)-cyclohexylidene]ethyl}diphenylphosphine oxide, (1R,3R,20S)-19-nor-2-methylene-1,3-bis(t-butyldimethylsilyloxy)-20-acetoxy-9,10-secopregna-5Z,7E-diene was produced.

Step 2:

Aqueous 3M sodium hydroxide solution (0.2 mL) was added to a tetrahydrofuran (5 mL)-methanol (5 mL) solution of (1R,3R,20S)-19-nor-2-methylene-1,3-bis(t-butyldimethylsilyloxy)-20-acetoxy-9,10-secopregna-5Z,7E-diene (140 mg) obtained in the above step 1, and then stirred at room temperature for 3 hours. Aqueous 3M sodium hydroxide solution (0.2 mL) was further added, stirred for 4 hours, then heated up to 45° C., and stirred for 13 hours. Tetrahydrofuran and methanol were removed by concentration under reduced pressure, then water was added thereto, and water solution was subjected to extraction twice with ether. The extract was washed with water and aqueous saturated sodium chloride solution, then dried over anhydrous magnesium sulfate, and concentrated under reduced pressure. The residue was purified through silica gel column chromatography to give (1R,3R,20S)-19-nor-2-methylene-1,3-bis(t-butyldimethylsilyloxy)-9,10-secopregna-5Z,7E-dien-20-ol (93 mg) as a colorless oil.

Step 3:

According to the same method as in the step 1 in Example 43 but using (1R,3R,20S)-19-nor-2-methylene-1,3-bis(t-butyldimethylsilyloxy)-9,10-secopregna-5Z,7E-dien-20-ol obtained in the above step 2. in place of (1R,3R,20S)-19-nor-1,3-bis(t-butyldimethylsilyloxy)-9,10-secopregna-5Z,7E-dien-20-ol, (1R,3R,20S)-19-nor-2-methylene-1,3-bis(t-butyldimethylsilyloxy)-20-(4-triethylsilyloxy-5,5,5-trifluoro-4-methylpentanoyloxy)-9,10-secopregna-5Z,7E-diene was produced.

Step 4:
(1R,3R,20S)-19-nor-2-methylene-1,3-bis(t-butyldimethylsilyloxy)-20-(4-triethylsilyloxy-5,5,5-trifluoro-4-methylpentanoyloxy)-9,10-secopregna-5Z,7E-diene was processed in the same manner as in the step 2 in Example 34 to give the entitled compound of the invention.
(+)-ESIMS m/z 501.6[M+1]$^+$, 523.4[M+Na]$^+$ Example 45

(1R,3R,20S)-2-methylene-19-nor-20-[(2E)-4-ethyl-4-hydroxyhex-2-enoyloxy]-9,10-secopregna-5Z,7E-diene-1,3-diol Step 1:
According to the same method as in the step 3 in Example 44 but using (2E)-4-triethylsilyloxy-4-ethylhex-2-enoic acid produced according to the method described in Non-Patent Reference 28 in place of 4-triethylsilyloxy-5,5,5-trifluoro-4-methylpentanoic acid, (1R,3R,20S)-19-nor-2-methylene-1,3-bis(t-butyldimethylsilyloxy)-20-[(2E)-4-ethyl-4-triethylsilyloxyhex-2-enoyloxy]-9,10-secopregna-5Z,7E-diene was produced.

Step 2:
(1R,3R,20S)-19-nor-2-methylene-1,3-bis(t-butyldimethylsilyloxy)-20-[(2E)-4-ethyl-4-triethylsilyloxyhex-2-enoyloxy]-9,10-secopregna-5Z,7E-diene obtained in the above step 1 was processed in the same manner as in the step 2 in Example 34 to give the entitled compound of the invention.
(+)-ESIMS m/z 473.4[M+1]$^+$, 495.6[M+Na]$^+$ Example 46

(1R,3R,20S)-19-nor-20-(4-hydroxy-4-methylpentanoyloxy)-9,10-secopregna-5Z,7E,16-triene-1,3-diol Step 1:
Under an argon atmosphere with cooling in an ice bath, sodium hydrogencarbonate (1.06g) and m-chloroperbenzoic acid (65%, 1.04g) were added to an anhydrous dichloromethane solution (50mL) of (Z)-des-A,B-8β-triethylsilyloxypregn-17(20)-ene (1.48g) produced according to Non-Patent Reference 47.. After stirred for 30 minutes, the solution was purified through silica gel column chromatography to give des-A,B-8β-triethylsilyloxy-17α,20α-epoxypregnane (858mg) as a colorless oil.

Step 2:
Under an argon atmosphere with cooling in an ice bath, a hexane solution (24.0ml) of 0.92. M diethylaluminium chloride was added to an anhydrous toluene solution (14mL) of 2.0M lithium diisopropylamide/heptane-tetrahydrofuran-ethylbenzene solution (16.6mL). After stirred for 1hour, a toluene solution (24mL) of des-A,B-8β-triethylsilyloxy-17α,20α-epoxypregnane (858mg) obtained in the above step 1was added thereto. After stirred further for 3.5hours, aqueous saturated sodium hydrogencarbonate solution was added thereto and filtered through Celite. This was subjected to extraction with ethyl acetate, the extract was dried over anhydrous magnesium sulfate, and concentrated under reduced pressure. The residue was purified through silica gel column chromatography to give (20S)-des-A,B-8β-triethylsilyloxypregn-6-en-20-ol (644mg) as a pale yellow oil.

Step 3:
According to the same method as in the step 1 in Example 34 but using 4-triethylsilyloxy-4-methylpentanoic acid (for example, its production method is described in Non-Patent Reference 25) in place of 5-triethylsilyloxy-5-ethylheptanoic acid and using (20S)-des-A,B-8β-triethylsilyloxypregn-16-en-20-ol obtained in the above step 2 in place of (1S,3R,20S)-1,3-bis(t-butyldimethylsilyloxy)-9,10-secopregna-5Z,7E,10(19)-trien-20-ol, (20S)-des-A,B-8β-triethylsilyloxy-20-(4-triethylsilyloxy-4-methylpentanoyloxy)pregn-16-ene was produced.

Step 4:
(20S)-des-A,B-8β-triethylsilyloxy-20-(4-triethylsilyloxy-4-methylpentanoyloxy)pregn-16-ene obtained in the above step 3 was processed in the same manner as in the step 2 in Example 34 to give (20S)-des-A,B-20-(4-hydroxy-4-methylpentanoyloxy)pregn-16-en-8β-ol.

Step 5:
According to the same method as in the step 3 in Example 40 but using (20S)-des-A,B-20-(4-hydroxy-4-methylpentanoyloxy)pregn-16-en-8β-ol obtained in the above step 4 in place of (20S)-des-A,B-20-(4-hydroxy-4-methylpentanoyloxy)pregnan-8β-ol, (20S)-des-A,B-20-(4-hydroxy-4-methylpentanoyloxy)pregn-16-en-8-one was produced.

Step 6:
According to the same method as in the step 4 in Example 40 but using (20S)-des-A,B-20-(4-hydroxy-4-methylpentanoyloxy)pregn-16-en-8-one obtained in the above step 5 in place of (20S)-des-A,B-20-(4-hydroxy-4-methylpentanoyloxy)pregnan-8-one, (20S)-des-A,B-20-(4-triethylsilyloxy-4-methylpentanoyloxy)pregn-16-en-8-one was produced.

Step 7:
According to the same method as in the step 5 in Example 40 but using (20S)-des-A,B-20-(4-triethylsilyloxy-4-methylpentanoyloxy)pregn-16-en-8-one obtained in the above step 6 in place of (20S)-des-A,B-20-(4-triethylsilyloxy-4-methylpentanoyloxy)pregnan-8-one, and using {2-[(3'R,5'R)-3',5'-bis(4-triethylsilyloxy)-cyclohexylidene]ethyl}diphenylphosphine oxide produced according to Non-Patent Reference 48in place of {2-[(3'R,5'R)-3',5'-bis(t-butyldimethylsilyloxy)-cyclohexylidene]ethyl}diphenylphosphine oxide, (1R,3R,20S)-19-nor-1,3-bis(triethylsilyloxy)-20-(4-triethylsilyloxy-4-methylpentanoyloxy)-9,10-secopregna-5Z,7E,16-triene was produced.

Step 8:
(1R,3R,20S)-19-nor-1,3-bis(triethylsilyloxy)-20-(4-triethylsilyloxy-4-methylpentanoyloxy)-9,10-secopregna-5Z,7E,16-triene obtained in the above step 7 was processed in the same manner as in the step 2 in Example 34 to give the entitled compound of the invention.
(+)-ESIMS m/z 455.4[M+Na]$^+$ Example 47

(1R,3R,20S)-19-nor-20-(5,5,5-trifluoro-4-hydroxy-4-methylpentanoyloxy)-9,10-secopregna-5Z,7E,16-triene-1,3-diol Step 1:
According to the same method as in the step 3 in Example 46 but using 4-triethylsilyloxy-5,5,5-trifluoro-4-methylpentanoic acid produced according to the method described in Non-Patent Reference 41in place of 4-triethylsilyloxy-4-methylpentanoic acid, (20S)-des-A,B-8β-(triethylsilyloxy)-20-(4-triethylsilyloxy-5,5,5-trifluoro-4-methylpentanoyloxy)pregn-16-ene was produced.

Step 2:

(20S)-des-A,B-8β-(triethylsilyloxy)-20-(4-triethylsilyloxy-5,5,5-trifluoro-4-methylpentanoyloxy)pregn-16-ene obtained in the above step 1. was processed in the same manner as in the step 2 in Example 34 to give (20S)-des-A,B-20-(5,5,5-trifluoro-4-hydroxy-4-methylpentanoyloxy)pregn-16-en-8β-ol.

Step 3:

According to the same method as in the step 3 in Example 40 but using (20S)-des-A,B-20-(5,5,5-trifluoro-4-hydroxy-4-methylpentanoyloxy)pregn-16-en-8β-ol obtained in the above step 2 in place of (20S)-des-A,B-20-(4-hydroxy-4-methylpentanoyloxy)pregnen-8β-ol, (20S)-des-A,B-20-(5,5,5-trifluoro-4-hydroxy-4-methylpentanoyloxy)pregn-16-en-8-one was produced.

Step 4:

According to the same method as in the step 4 in Example 40 but using (20S)-des-A,B-20-(5,5,5-trifluoro-4-hydroxy-4-methylpentanoyloxy)pregn-16-en-8-one obtained in the above step 3 in place of (20S)-des-A,B-20-(4-hydroxy-4-methylpentanoyloxy)pregnan-8-one, and using chlorotrimethylsilane in place of chlorotriethylsilane, (20S)-des-A,B-20-(5,5,5-trifluoro-4-trimethylsilyloxy-4-methylpentanoyloxy)pregn-16-en-8-one was produced.

Step 5:

According to the same method as in the step 5 in Example 40 but using (20S)-des-A,B-20-(5,5,5-trifluoro-4-trimethylsilyloxy-4-methylpentanoyloxy)pregn-16-en-8-one obtained in the above step 4 in place of (20S)-des-A,B-20-(4-triethylsilyloxy-4-methylpentanoyloxy)pregnan-8-one, and using {2-[(3'R,5'R)-3',5'-bis(triethylsilyloxy)-cyclohexylidene]ethyl}diphenylphosphine oxide produced according to Non-Patent Reference 48 in place of {2-[(3'R,5'R)-3',5'-bis(t-butyldimethylsilyloxy)-cyclohexylidene]ethyl}diphenylphosphine oxide, (1R,3R,20S)-19-nor-1,3-bis(triethylsilyloxy)-20-(5,5,5-trifluoro-4-trimethylsilyloxy-4-methylpentanoyloxy)-9,10-secopregna-5Z,7E,16-triene was produced.

Step 6:

(1R,3R,20S)-19-nor-1,3-bis(triethylsilyloxy)-20-(5,5,5-trifluoro-4-trimethylsilyloxy-4-methylpentanoyloxy)-9,10-secopregna-5Z,7E,16-triene obtained in the above step 5 was processed in the same manner as in the step 2 in Example 1 to give the entitled compound of the invention.

(+)-ESIMS m/z 509.4[M+Na]$^+$

Example 48

(1R,3R,20S)-19-nor-2-methylene-20-(4-hydroxy-4-methylpentanoyloxy)-9,10-secopregna-5Z,7E,16-triene-1,3-diol Step 1:

According to the same method as in the step 7 in Example 46 but using 2-[(3'R,5'R)-3',5'-bis(triethylsilyloxy)-4'-methylenecyclohexylidene]ethyl}diphenylphosphine oxide produced according to Non-Patent Reference 49 in place of {2-[(3'R,5'R)-3',5'-bis(triethylsilyloxy)-cyclohexylidene]ethyl}diphenylphosphine oxide, (1R,3R,20S)-19-nor-2-methylene-1,3-bis(triethylsilyloxy)-20-(4-triethylsilyloxy-4-methylpentanoyloxy)-9,10-secopregna-5Z,7E,16-triene was produced.

Step 2:

(1R,3R,20S)-19-nor-2-methylene-1,3-bis(triethylsilyloxy)-20-(4-triethylsilyloxy-4-methylpentanoyloxy)-9,10-secopregna-5Z,7E,16-triene was processed in the same manner as in the step 2. in Example 34 to give the entitled compound of the invention.

(+)-ESIMS m/z 445.4[M+1]$^+$, 467.4[M+Na]$^+$

Example 49

(1S,3R,20S)-20-(5,5,5-trifluoro-4-hydroxy-4-methylpentanoyloxy)-9,10-secopregna-5Z,7E,10(19),16-tetraene-1,3-diol Step 1:

According to the same method as in the step 5 in Example 47 but using [3'S-(1'Z,3β,5α)]{2-[3',5'-bis(triethylsilyloxy)-2'-methylenecyclohexylidene]ethyl}diphenylphosphine oxide produced according to Non-Patent Reference 50 in place of {2-[(3'R,5'R)-3',5'-bis(triethylsilyloxy)-cyclohexylidene]ethyl}diphenylphosphine oxide, (1S,3R,20S)-1,3-bis(triethylsilyloxy)-20-[5,5,5-trifluoro-4-(trimethylsilyloxy)-4-methylpentanoyloxy]-9,10-secopregna-5Z,7E,10(19),16-tetraene was produced.

Step 2:

(1S,3R,20S)-1,3-bis(triethylsilyloxy)-20-[5,5,5-trifluoro-4-(trimethylsilyloxy)-4-methylpentanoyloxy]-9,10-secopregna-5Z,7E,10(19),16-tetraene obtained in the above step 1 was processed in the same manner as in the step 2 in Example 34 to give the entitled compound of the invention.

(+)-ESIMS m/z 521.4[M+Na]$^+$

Example 50

(1R,2α,3R,20S)-2-methyl-19-nor-20-(4-hydroxy-4-methylpentanoyloxy)-9,10-secopregna-5Z,7E-diene-1,3-diol Anhydrous benzene (10. mL) was saturated with hydrogen gas, then tris(triphenylphosphine)rhodium chloride (34 mg) was added, and stirred to give a uniform solution. An anhydrous benzene solution (1 mL) of (1R,3R,20S)-2-methylene-19-nor-20-(4-hydroxy-4-methylpentanoyloxy)-9,10-secopregna-5Z,7E-diene-1,3-diol (8 mg) obtained in Example 41 was added, stirred for 1.5 hours, then purged with argon and concentrated under reduced pressure. The residue was purified through silica gel column chromatography, and then fractionated through high-performance liquid chromatography [YMC Pack ODS-AM (150×20mm ID), 50% acetonitrile-water, 10ml/min, UV 254nm] The solution containing the compound that had been eluted later was concentrated and purified to give the entitled compound (1.9 mg) of the invention as a colorless powder.

$^1$H-NMR (CDCl$_3$) δ: 0.54(3H, s), 1.13(3H, d, J=7.0Hz), 1.23(6H, s), 1.23(3H, d, J=6.2Hz), 2.39(2H, t, J=8.0 Hz), 2.60(1H, dd, J=13.2Hz, J=4.0Hz), 2.79(1H, dd, J=13.2Hz, J=5.0Hz), 3.62(1H, dt, J=9.2Hz, J=4.4Hz), 3.97(1H, brs), 4.95(1H, quint, J=6.2Hz), 5.83(1H, d, J=11.2Hz), 6.36(1H, d, 11.2Hz)

(+)-ESIMS m/z 449.4[M+1]$^+$, 471.4[M+Na]$^+$

Example 51

(1R,2β,3R,20S)-2-methyl-19-nor-20-(4-hydroxy-4-methylpentanoyloxy)-9,10-secopregna-5Z,7E-diene-1,3-diol In the fractionation step with high-performance liquid chromatography in Example 50, the solution containing the compound that had been eluted first was concentrated and purified to give the entitled compound (2.1mg) of the invention as a colorless powder.

$^1$H-NMR (CDCl$_3$) δ: 0.55(3H, s), 1.15(3H, d, J=6.6Hz), (6H, s), 1.24(3H, d, J=6.2Hz), 2.40(2H, t, J=7.2Hz), (1H, d, J=10Hz), 3.08(1H, dd, J=13.6Hz, J=4.0Hz), (1H, m), 3.91 (1H, brs), 4.96(1H, quint, J=6.2Hz), 5.88(1H, d, J=10.9Hz), 6.25(1H, d, 10.9Hz)

(+)-ESIMS m/z 449.4[M+1]$^+$, 471.4[M+Na]$^+$

Example 52

(1R,3R,20S)-2-methyl-19-nor-20-(5,5,5-trifluoro-4-hydroxy-4-methylpentanoyloxy)-9,10-secopregna-5Z,7E-diene-1,3-diol According to the same method as in Example 50but using (1R,3R,20S)-2-methylene-19-nor-20-(5,5,5-trifluoro-4-hydroxy-4-methylpentanoyloxy)-9,10-secopregna-5Z,7E-diene-1,3-diol produced in Example 44. in place of (1R,3R, 20S)-2-methylene-19-nor-20-(4-hydroxy-4-methylpentanoyloxy)-9,10-secopregna-5Z,7E-diene-1,3-diol, the entitled compound of the invention was produced.

(+)-ESIMS m/z 525.4. [M+Na]$^+$

Example 53

(1R,3R,20S)-2-methyl-19-nor-20-[(2E)-4-ethyl-4-hydroxyhex-2-enoyloxy]-9,10-secopregna-5Z,7E-diene-1,3-diol According to the same method as in Example 50but using (1R,3R,20S)-2-methylene-19-nor-20-[(2E)-4-ethyl-4-hydroxyhex-2-enoyloxy]-9,10-secopregna-5Z,7E-diene-1,3-diol produced in Example 45in place of (1R,3R,20S)-2-methylene-19-nor-20-(4-hydroxy-4-methylpentanoyloxy)-9,10-secopregna-5Z,7E-diene-1,3-diol, the entitled compound of the invention was produced.

EIMS m/z 474. M$^+$

Example 54

(1R,3R,20S)-19-nor-2-methyl-20-(4-hydroxy-4-methylpentanoyloxy)-9,10-secopregna-5Z,7E,16-triene-1,3-diol According to the same method as in Example 50but using (1R,3R,20S)-19-nor-2-methylene-20-(4-hydroxy-4-methylpentanoyloxy)-9,10-secopregna-5Z,7E,16-triene-1,3-diol produced in Example 48in place of (1R,3R,20S)-2-methylene-19-nor-20-(4-hydroxy-4-methylpentanoyloxy)-9,10-secopregna-5Z,7E-diene-1,3-diol, the entitled compound of the invention was produced.

(+)-ESIMS 469.4[M+Na]$^+$

Example 55

(1R,3R,20S)-19-nor-2-methylene-20-[(4S)-5,5,5-trifluoro-4-hydroxy-4-methylpentanoyloxy]-9,10-secopregna-5Z,7E,16-triene-1,3-diol Step 1:
According to the same method as in the step 1in Example 48but using (20S)-des-A,B-20-[5,5,5-trifluoro-4-(trimethylsilyloxy)-4-methylpentanoyloxy]pregn-16-en-8-one obtained in the step 4in Example 47in place of (20S)-des-A,B-20-(4-triethylsilyloxy-4-methylpentanoyloxy)pregn-16-en-8-one, (1R,3R,20S)-19-nor-2-methylene-1,3-bis(triethylsilyloxy)-20-[5,5,5-trifluoro-4-(trimethylsilyloxy)-4-methylpentanoyloxy]-9,10-secopregna-5Z,7E,16-triene was produced.

Step 2:
(1R,3R,20S)-19-nor-2-methylene-1,3-bis(triethylsilyloxy)-20-[5,5,5-trifluoro-4-(trimethylsilyloxy)-4-methylpentanoyloxy]-9,10-secopregna-5Z,7E,16-triene obtained in the step 1was processed in the same manner as in the step 2in Example 34, and further fractionated through high-performance liquid chromatography [DAICEL CHIRALPAK AD (20×250mm ID), 15% isopropanol-hexane, 8ml/min, UV 254nm]. The solution containing the compound that had been eluted first was concentrated and purified to give the entitled compound of the invention.

(+)-ESIMS m/z 521.4[M+Na]$^+$ $^1$H-NMR (CDCl$_3$) δ: 0.784(3H, s), 1.333(3H, s), 1.385 (3H, d, J=6.6Hz), 2.83(2H, m), 3.23(1H, brs), 4.49(2H, m), 5.12 (2H, d, J=4.0Hz), 5.478(1H, q, 6.6Hz), 5.71(1H, brs), 5.975(1H, d, J=11.0Hz), 6.344(1H, d, J=11.0Hz)

Example 56

(1R,3R,20S)-19-nor-2-methylene-20-[(4R)-5,5,5-trifluoro-4-hydroxy-4-methylpentanoyloxy]-9,10-secopregna-5Z,7E,16-triene-1,3-diol In the step of fractionation through high-performance liquid chromatography in Example 55, the solution containing the compound that had been eluted later was concentrated and purified to give the entitled compound of the invention.

(+)-ESIMS m/z 521.4[M+Na]$^+$ $^1$H-NMR (CDCl$_3$) δ: 0.782(3H, s), 1.335(3H, s), 1.383 (3H, d, J=6.6Hz), 2.83(2H, m), 4.51(2H, m), 5.11(2H, d, J=4.0 Hz), 5.475(1H, q, 6.6Hz), 5.71(1H, brs), 5.976(1H, d, J=11.4Hz), 6.345(1H, d, J=11.4Hz)

Example 57

(1R,3R,20S)-2-methylene-19-nor-20-(5-hydroxy-5-methylhexanoyloxy)-9,10-secopregna-5Z,7E-diene-1,3-diol Step 1:
According to the same method as in the step 3in Example 44but using 5-triethylsilyloxy-5-methylhexanoic acid produced according to the method described in Non-Patent Reference 26in place of 4-triethylsilyloxy-5,5,5-trifluoro-4-methylpentanoic acid, (1R,3R,20S)-19-nor-2-methylene-1,3-bis(t-butyldimethylsilyloxy)-20-(5-triethylsilyloxy-5-methylhexanoyloxy)-9,10-secopregna-5Z,7E-diene was produced.

Step 2:
(1R,3R,20S)-19-nor-2-methylene-1,3-bis(t-butyldimethylsilyloxy)-20-(5-triethylsilyloxy-5-methylhexanoyloxy)-9,10-secopregna-5Z,7E-diene obtained in the above step 1was processed in the same manner as in the step 2in Example 34to give the entitled compound of the invention.

(+)-ESIMS m/z 461.4[M+1]$^+$, 483.4[M+Na]$^+$, 499.5[M+K]$^+$

Example 58

(1R,2α,3R,20S)-2-methyl-19-nor-20-(5-hydroxy-5-methylhexanoyloxy)-9,10-secopregna-5Z,7E-diene-1,3-diol Step 1:

According to the same method as in Example 50 but using (1R,3R,20S)-2-methylene-19-nor-20-(5-hydroxy-5-methylhexanoyloxy)-9,10-secopregna-5Z,7E-diene-1,3-diol produced in Example 57 in place of (1R,3R,20S)-2-methylene-19-nor-20-(4-hydroxy-4-methylpentanoyloxy)-9,10-secopregna-5Z,7E-diene-1,3-diol, and concentrating and purifying the solution containing the compound that had been eluted later in the step of fractionation through high-performance liquid chromatography, the entitled compound of the invention was produced.

$^1$H-NMR (CDCl$_3$) δ: 0.54(3H, s), 1.13(3H, d, J=6.6Hz), 1.23(3H, d, J=6.2Hz), 1.23(6H, s), 2.28(2H, t, J=7.4 Hz), 2.60(1H, dd, J=13.0, 4.0Hz), 2.80(2H, m), 3.63(1H, m), 3.97(1H, brs), 4.95(1H, quint, J=6.2Hz), 5.83(1H, d, J=11.2Hz), 6.36(1H, d, J=11.2Hz)

(+)-ESIMS m/z 463.4[M+1]$^+$, 485.4[M+Na]$^+$, 501.4[M+K]$^+$

Example 59

(1R,2β,3R,20S)-2-methyl-19-nor-20-(5-hydroxy-5-methylhexanoyloxy)-9,10-secopregna-5Z,7E-diene-1,3-diol Step 1:

In the step of fractionation through high-performance liquid chromatography in Example 58, the solution containing the compound that had been eluted first was concentrated and purified to give the entitled compound of the invention.

$^1$H-NMR (CDCl$_3$) δ: 0.55(3H, s), 1.14(3H, d, J=6.6Hz), 1.23(3H, d, J=6.2Hz), 1.23(6H, s), 2.29(2H, t, J=7.4 Hz), 2.37(2H, m), 2.81(1H, m), 3.07(1H, dd, J=12.6, 4.4 Hz), 3.51(1H, m), 3.91(1H, brs), 4.96(1H, quint, J=6.2 Hz), 5.88(1H, d, J=11.2Hz), 6.25(1H, d, J=11.2Hz)

(+)-ESIMS m/z 463.3[M+1]$^+$, 485.5[M+Na]$^+$, 501.5[M+K]$^+$

Example 60

(1R,2α,3R,20S)-2-methyl-19-nor-20-(5,5,5-trifluoro-4-hydroxy-4-methylpentanoyloxy)-9,10-secopregna-5Z,7E-diene-1,3-diol (1R,2α,3R,20S)-19-nor-20-(4-hydroxy-5,5,5-trifluoro-4-methylpentanoyloxy)-9,10-secopregna-5Z,7E-diene-1,3-diol obtained in Example 52 was purified through high-performance liquid chromatography [YMC Pack ODS-AM (150×20mm ID), 55% acetonitrile-water, 10ml/min, UV 254nm], and the solution containing the compound that had been eluted later was concentrated and purified to give the entitled compound of the invention.

$^1$H-NMR (CDCl$_3$) δ: 0.54(3H, s), 1.13(3H, d, J=7.0Hz), 1.25(3H, d, J=6.0Hz), 1.335(3H, s), 2.51(2H, t, J=7.0 Hz), 2.80(2H, m), 3.65(1H, m), 3.97(1H, brs), 4.98(1H, quint, J=6.0Hz), 5.83(1H, d, J=11.2Hz), 6.36(1H, d, J=11.2Hz)

Example 61

(1R,2β,3R,20S)-2-methyl-19-nor-20-(5,5,5-trifluoro-4-hydroxy-4-methylpentanoyloxy)-9,10-secopregna-5Z,7E-diene-1,3-diol In the step of fractionation through high-performance liquid chromatography in Example 60, the solution containing the compound that had been eluted first was concentrated and purified to give the entitled compound of the invention.

$^1$H-NMR (CDCl$_3$) δ: 0.55(3H, s), 1.15(3H, d, J=7.0Hz), 1.25(3H, d, J=6.0Hz), 1.338(3H, s), 2.51(2H, t, J=7.0 Hz), 2.82(1H, d, J=12.0Hz), 3.08(1H, dd, J=12.0, 4.4Hz), 3.51(1H, m), 3.91(1H, brs), 4.98(1H, quint, J=6.0Hz), 5.88(1H, d, J=11.2Hz), 6.25(1H, d, J=11.2Hz)

Example 62

(1R,2α,3R,20S)-19-nor-2-methyl-20-(4-hydroxy-4-methylpentanoyloxy)-9,10-secopregna-5Z,7E,16-triene-1,3-diol (1R,3R,20S)-2-methyl-19-nor-20-(4-hydroxy-4-methylpentanoyloxy)-9,10-secopregna-5Z,7E,16-triene-1,3-diol obtained in Example 54 was purified through high-performance liquid chromatography in the same manner as in Example 50, and the solution containing the compound that had been eluted later was concentrated and purified to give the entitled compound of the invention.

(+)-ESIMS m/z 469.4[M+Na]$^+$ $^1$H-NMR (CDCl$_3$) δ: 0.77(3H, s), 1.14(3H, d, J=6.6Hz), 1.23(6H, s), 1.37(3H, d, J=6.2Hz), 1.82(2H, t, J=8.0 Hz), 2.43(2H, t, J=8.0Hz), 2.61(1H, dd, J=12.6, 4.4Hz), 2.80(1H, dd, J=14.0, 4.8Hz), 3.63(1H, m), 3.97(1H, m), 5.46(1H, q, J=6.2Hz), 5.70(1H, brs), 5.91(1H, d, J=11.2 Hz), 6.36(1H, d, J=11.2Hz)

Example 63

(1R,2β,3R,20S)-19-nor-2-methyl-20-(4-hydroxy-4-methylpentanoyloxy)-9,10-secopregna-5Z,7E,16-triene-1,3-diol In the step of fractionation through high-performance liquid chromatography in Example 62, the solution containing the compound that had been eluted first was concentrated and purified to give the entitled compound of the invention.

(+)-ESIMS m/z 469.4[M+Na]$^+$ $^1$H-NMR (CDCl$_3$) δ: 0.78(3H, s), 1.15(3H, d, J=6.6Hz), 1.23(6H, s), 1.37(3H, d, J=6.2Hz), 1.82(2H, t, J=8.0 Hz), 2.44(2H, t, J=8.0Hz), 2.79(1H, brd, J=9.6Hz), 3.09 (1H, dd, J=12.3, 4.6Hz), 3.53(1H, m), 3.91(1H, brs), 5.47(1H, q, J=6.6Hz), 5.71(1H, brs), 5.96(1H, d, J=11.2 Hz), 6.25(1H, d, J=11.2Hz)

Example 64

(1R,2β,3R,20S)-2-methyl-19-nor-20-[(2E)-4-ethyl-4-hydroxyhex-2-enoyloxy]-9,10-secopregna-5Z,7E-diene-1,3-diol (1R,3R,20S)-2-methyl-19-nor-20-[(2E)-4-ethyl-4-hydroxyhex-2-enoyloxy]-9,10-secopregna-5Z,7E-diene-1,3-diol obtained in Example 53 was purified through high-performance liquid chromatography [YMC Pack ODS-AM (150×20mm ID), 55% acetonitrile-water, 10ml/min, UV 254nm]. The solution containing the compound that had been eluted first was concentrated, and was further fractionated through HPLC [CHIRALPAK AD (20×250mm ID), Hex-EtOH=80:20, 10ml/min, UV 254nm]. The solution containing the compound that had been eluted first was concentrated and purified to give the entitled compound (1.8mg) of the invention.

(+)-ESIMS m/z 497.4[M+Na]$^+$, 475.3[M+1]$^+$
$^1$H-NMR (CDCl$_3$) δ: 0.56(3H, s), 0.88(6H, t, J=7.2Hz), 1.15(3H, d, J=6.6Hz), 1.28(3H, d, J=7.0Hz), 2.38(2H, m), 2.81(1H, brd, J=14.0Hz), 3.09(1H, dd, J=12.4, 4.6 Hz), 3.52 (1H, td, J=10.1, 4.4Hz), 3.91(1H, brs), 5.02 (1H, quint, J=6.2Hz), 5.88(1H, d, J=11.2Hz), 6.00(1H, d, J=15.8Hz), 6.25(1H, d, J=11.2Hz), 6.85(1H, d, J=15.8 Hz)

Example 65

(1R,2α,3R,20S)-2-methyl-19-nor-20-[(2E)-4-ethyl-4-hydroxyhex-2-enoyloxy]-9,10-secopregna-5Z,7E-diene-1,3-diol (1R,3R,20S)-2-methyl-19-nor-20-[(2E)-4-ethyl-4-hydroxyhex-2-enoyloxy]-9,10-secopregna-5Z,7E-diene-1,3-diol obtained in Example 53. was purified through high-performance liquid chromatography [YMC Pack ODS-AM (150×20mm ID), 55% acetonitrile-water, 10ml/min, UV 254nm]. The solution containing the compound that had been eluted later was concentrated, and was further partitioned through HPLC [CHIRALPAK AD (20×250mm ID), Hex-EtOH=80:20, 10 ml/min, UV 254nm]. The solution containing the compound that had been eluted first was concentrated and purified to give the entitled compound (2.2mg) of the invention.

(+)-ESIMS m/z 497.5[M+Na]$^+$, 475.3. [M+1]$^+$
$^1$H-NMR (CDCl$_3$) δ: 0.55(3H, s), 0.88(6H, t, J=7.2Hz), 1.13(3H, d, J=6.6Hz), 1.27(3H, d, J=7.0Hz), 2.60. (1H, dd, J=13.2, 4.4Hz), 2.79(2H, m), 3.62(1H, td, J=9.2, 4.8 Hz), 3.95(1H, brs), 5.02(1H, quint, J=6.2Hz), 5.84. (1H, d, J=11.2Hz), 5.99(1H, d, J=15.2Hz), 6.36(1H, d, J=11.2 Hz), 6.85(1H, d, J=15.2Hz)

Example 66

(1R,2β,3R,20S)-2-methyl-19-nor-20-[4-ethyl-4-hydroxyhexanoyloxy]-9,10-secopregna-5Z,7E-diene-1,3-diol Anhydrous benzene (10mL) was saturated with hydrogen gas, then tris(triphenylphosphine)rhodium chloride (39mg) was added, and stirred to give a uniform solution. An anhydrous benzene solution (3mL) of (1R,3R,20S)-2-methylene-19-nor-20-[(2E)-4-ethyl-4-hydroxyhex-2-enoyloxy]-9,10-secopregna-5Z,7E-diene-1,3-diol (10mg) obtained in Example 45. was added, stirred for 1hour, then purged with argon and concentrated under reduced pressure. The residue was purified through silica gel column chromatography, and then fractionated through high-performance liquid chromatography [YMC Pack ODS-AM (150×20mm ID), 55% acetonitrile-water, 10ml/min, UV 254nm]. The solution containing the compound that had been eluted first was concentrated, and further, fractionated through HPLC [CHIRALPAK AD (20×250mm ID), Hex-EtOH=80:20, 10ml/min, UV 254nm]. The solution containing the compound that had been eluted later was concentrated and purified to give the entitled compound (0.9mg) of the invention as a colorless powder.

(+)-ESIMS m/z 499.5[M+Na]$^+$, 477.4[M+1]$^+$
$^1$H-NMR (CDCl$_3$) δ: 0.55(3H, s), 0.87(6H, t, J=7.2Hz), 1.15(3H, d, J=6.6Hz), 1.24(3H, d, J=7.0Hz), 2.34. (2H, t, J=7.0Hz), 2.82(1H, brd, J=11.0Hz), 3.09(1H, m), 3.51 (1H, m), 3.92(1H, brs), 4.95(1H, quint, J=6.2Hz), 5.88 (1H, d, J=11.2Hz), 6.25(1H, d, J=11.2Hz)

Example 67

(1R,2α,3R,20S)-2-methyl-19-nor-20-[4-ethyl-4-hydroxyhexanoyloxy]-9,10-secopregna-5Z,7E-diene-1,3-diol Anhydrous benzene (10mL) was saturated with hydrogen gas, then tris(triphenylphosphine)rhodium chloride (39mg) was added, and stirred to give a uniform solution. An anhydrous benzene solution (3mL) of (1R,3R,20S)-2-methylene-19-nor-20-[(2E)-4-ethyl-4-hydroxyhex-2-enoyloxy]-9,10-secopregna-5Z,7E-diene-1,3-diol (10mg) obtained in Example 45. was added, stirred for 1hour, then purged with argon and concentrated under reduced pressure. The residue was purified through silica gel column chromatography, and then fractionated through high-performance liquid chromatography [YMC Pack ODS-AM (150×20mm ID), 55% acetonitrile-water, 10ml/min, UV 254nm]. The solution containing the compound that had been eluted later was concentrated, And further fractionated through HPLC [CHIRALPAK AD (20×250mm ID), Hex-EtOH=80:20, 10ml/min, UV 254nm]. The solution containing the compound that had been eluted later was concentrated and purified to give the entitled compound (1.0mg) of the invention as a colorless powder.

(+)-ESIMS m/z 499.5[M+Na]$^+$, 477.4[M+1]$^+$
$^1$H-NMR (CDCl$_3$) δ: 0.54(3H, s), 0.87(6H, t, J=7.2Hz), 1.13(3H, d, J=6.6Hz), 1.24(3H, d, J=7.0Hz), 2.33(2H, t, J=7.0Hz), 2.60(1H, dd, J=13.2, 4.4Hz), 2.80(2H, m), 3.63 (1H, m), 3.97(1H, brs), 4.95(1H, quint, J=6.2Hz), 5.83(1H, d, J=11.2Hz), 6.36(1H, d, J=11.2Hz)

Example 68

(1R,3R,20S)-19-nor-20-[(4S)-5,5,5-trifluoro-4-hydroxy-4-methylpentanoyloxy]-9,10-secopregna-5Z,7E,16-triene-1,3-diol (1R,3R,20S)-19-nor-20-(5,5,5-trifluoro-4-hydroxy-4-methylpentanoyloxy)-9,10-secopregna-5Z,7E,16-triene-1,3-diol obtained in Example 47was fractionated through high-performance liquid chromatography [DAICEL CHIRALPAK AD (20×250mm ID), 15% isopropanol-hexane, 8ml/min, UV 254nm]. The solution containing the compound that had been eluted first was concentrated and purified to give the entitled compound of the invention.

(+)-ESIMS m/z 509.4[M+Na]$^+$
1H-NMR (CDCl$_3$) δ: 0.78(3H, s), 1.335(3H, s), 1.38(3H, d, J=6.2Hz), 2.77(2H, m), 4.12(2H, m), 5.47(1H, q, J=6.2 Hz), 5.71(1H, brs), 5.94(1H, d, J=11.2Hz), 6.30(1H, d, J=11.2Hz)

Example 69

(1R,3R,20S)-19-nor-20-[(4R)-5,5,5-trifluoro-4-hydroxy-4-methylpentanoyloxy]-9,10-secopregna-5Z,7E,16-triene-1,3-diol In the step of fractionation through high-performance liquid chromatography in Example 68, the solution containing the compound that had been eluted later was concentrated to give the entitled compound of the invention.

1H-NMR (CDCl$_3$) δ: 0.78(3H, s), 1.338(3H, s), 1.38(3H, d, J=6.2Hz), 2.77(2H, m), 4.12(2H, m), 5.48(1H, q, J=6.2 Hz), 5.71(1H, brs), 5.95(1H, d, J=11.2Hz), 6.30(1H, d, J=11.2Hz)

Example 70

(1S,3R,20S)-20-[(4R) or (4S)-5,5,5-trifluoro-4-hydroxy-4-methylpentanoyloxy]-9,10-secopregna-5Z, 7E,10(19),16-tetraene-1,3-diol (1S,3R,20S)-20-(5,5,5-trifluoro-4-hydroxy-4-methylpentanoyloxy)-9,10-secopregna-5Z,7E,10(19),16-tetraene-1,3-diol obtained in Example 49was fractionated through high-performance liquid chromatography [CHIRALPAK AD (20× 250mm ID), Hex-i-PrOH=90:10, 10ml/min, UV 254 nm]. The solution containing the compound that had been eluted first was concentrated and purified to give the entitled compound (3mg) of the invention as a colorless powder.

(+)-ESIMS m/z 521.4. [M+Na]$^+$
$^1$H-NMR (CDCl$_3$) δ: 0.771(3H, s), 1.33(3H, s), 1.37(3H, d, J=6.2Hz), 2.53(2H, t, J=6.8Hz), 2.82(1H, m), 3.18(1H, brs), 4.24(1H, m), 4.42(1H, m), 5.00(1H, brs), 5.33(1H, brs), 5.46 (1H, q, 6.2Hz), 5.67(1H, brs), 6.10(1H, d, J=11.2Hz), 6.36 (1H, d, J=11.2Hz)

Example 71

(1S,3R,20S)-20-[(4S) or (4R)-5,5,5-trifluoro-4-hydroxy-4-methylpentanoyloxy]-9,10-secopregna-5Z, 7E,10(19),16-tetraene-1,3-diol In the step of fractionation through high-performance liquid chromatography in Example 70, the solution containing the compound that had been eluted later was concentrated to give the entitled compound of the invention.

(+)-ESIMS m/z 521.4[M+Na]$^+$
$^1$H-NMR (CDCl$_3$) δ: 0.773(3H, s), 1.34(3H, s), 1.37(3H, d, J=6.2Hz), 2.57(2H, t, J=7.0Hz), 2.82(1H, m), 3.19(1H, brs), 4.24(1H, m), 4.42(1H, m), 5.00(1H, brs), 5.34(1H, brs), 5.46 (1H, q, 6.2Hz), 5.68(1H, brs), 6.10(1H, d, J=11.0Hz), 6.36 (1H, d, J=11.0Hz)

Example 72

(1R,3R,20S)-19-nor-20-[(4S)-5,5,5-trifluoro-4-hydroxy-4-methylpentanoyloxy]-9,10-secopregna-5Z, 7E-diene-1,3-diol (1R,3R,20S)-19-nor-20-(5,5,5-trifluoro-4-hydroxy-4-methylpentanoyloxy)-9,10-secopregna-5Z,7E-diene-1,3-diol obtained in Example 43. was fractionated through high-performance liquid chromatography [DAICEL CHIRALPAK AD (20×250mm ID), 10% ethanol-hexane, 10ml/min, UV 254nm]. The solution containing the compound that had been eluted first was concentrated to give the entitled compound of the invention.

(+)-ESIMS m/z 489.3. [M+1]$^+$, 511.3[M+Na]$^+$
$^1$H-NMR (CDCl$_3$) δ: 0.54(3H, s), 1.24(3H, d, J=7.0Hz), (3H, s), 2.50(2H, m), 2.78(1H, m), 3.30(1H, brs), 4.05(2H, m), 4.97(1H, quint, 7.0Hz), 5.86(1H, d, J=11.6 Hz), 6.30(1H, d, J=11.6Hz)

Example 73

(1R,3R,20S)-19-nor-20-[(4R)-5,5,5-trifluoro-4-hydroxy-4-methylpentanoyloxy]-9,10-secopregna-5Z, 7E-diene-1,3-diol In the step of fractionation through high-performance liquid chromatography in Example 72, the solution containing the compound that had been eluted later was concentrated to give the entitled compound of the invention.

(+)-ESIMS m/z 489.4[M+1]$^+$, 511.4[M+Na]$^+$
$^1$H-NMR (CDCl$_3$) δ: 0.55(3H, s), 1.24(3H, d, J=6.6Hz), (3H, s), 2.51(2H, m), 2.78(1H, m), 4.07(2H, m), (1H, quint, 6.6Hz), 5.81(1H, d, J=11.0Hz), 6.30(1H, d, J=11.0Hz)

Test Example 1

Investigation of the Ability to Induce Differentiation of Human Acute Myelogenous Leukemia Cell Line HL-60

It is known that the human acute myelogenous leukemia cell line HL-60is differentiated into neutrophil-like cells by active vitamin D or the like. Thus, the cells after the differentiation begin to express a surface marker such as CD11and CD32and, at the same time, they produce an oxygen radical by stimulation with a phorbol ester or the like. In this test, the above-mentioned property was utilized. As an index of the ability to induce differentiation of the HL-60cells, the amount of the oxygen radical produced by stimulation with a phorbol ester was measured, and the compounds of the invention mentioned in Examples were compared with maxacalcitol with respect to the vitamin D3activity thereof. In use of commercial reagents and kits, if any, the indications attached thereto were referred to.
(Process)
HL-60cells (supplied from ATCC) were seeded on a 96-well plate at 5×10$^3$cells/100μL/well and a test compound in two-fold dilution series from 10$^{-7}$M was added to the second to the twelfth rows (maximum concentration: the second row). The first row was used for blank. After incubation for 72 hours under a moisturized condition in the presence of 5% CO$_2$ at 37° C. using a CO$_2$ incubator, 10 μL of PBS containing 50 mM WST-1 (manufactured by Takara Bio) and 10 μM phorbol 12,13-didecanoate (manufactured by SIGMA) were added to each well followed by further incubation for 4 hours. Absorbance (reference wavelength: 655 nM) at 450 nM of the WST-1 formazane dye generated by conversion from WST-1 by oxygen radical produced from the differentiated HL-60 cells was measured by a Benchmark microplate reader (manufactured by BioRad). An absorbance meter control software MPM3 (manufactured by BioRad) was used and, from a concentration-absorbance curve, the 50%-maximal effective concentration (hereinafter, referred to as "EC$_{50}$") of each was determined by a logistic curve regression. The result is shown in Table 1.

TABLE 1

| Test Compound | EC50 (nM) |
|---|---|
| Maxacalcitol | 5.4 |
| Compound of Example 1 | 1.5 |
| Compound of Example 3 | 4.5 |
| Compound of Example 4 | 0.31 |
| Compound of Example 5 | 0.86 |
| Compound of Example 7 | 0.38 |
| Compound of Example 8 | 3.4 |

TABLE 1-continued

| Test Compound | EC50 (nM) |
|---|---|
| Compound of Example 10 | 0.99 |
| Compound of Example 11 | 2.2 |
| Compound of Example 12 | 1.5 |
| Compound of Example 13 | 0.53 |
| Compound of Example 19 | 2.4 |
| Compound of Example 20 | 1.4 |
| Compound of Example 27 | 4.1 |
| Compound of Example 28 | 1.7 |
| Compound of Example 34 | 4.2 |
| Compound of Example 35 | 0.82 |
| Compound of Example 36 | 0.41 |
| Compound of Example 37 | 1.1 |
| Compound of Example 38 | 2.3 |
| Compound of Example 39 | 1.4 |
| Compound of Example 40 | 1.6 |
| Compound of Example 41 | 0.26 |
| Compound of Example 42 | 1.3 |
| Compound of Example 43 | 0.45 |
| Compound of Example 44 | 0.25 |
| Compound of Example 45 | 0.31 |
| Compound of Example 46 | 1.4 |
| Compound of Example 47 | 0.63 |
| Compound of Example 48 | 0.21 |
| Compound of Example 50 | 0.043 |
| Compound of Example 55 | 0.15 |
| Compound of Example 56 | 0.47 |
| Compound of Example 57 | 0.53 |
| Compound of Example 58 | 0.53 |
| Compound of Example 60 | 0.053 |
| Compound of Example 61 | 1.2 |
| Compound of Example 62 | 0.23 |
| Compound of Example 65 | 0.29 |
| Compound of Example 67 | 0.15 |
| Compound of Example 68 | 0.23 |
| Compound of Example 69 | 0.77 |
| Compound of Example 70 | 0.13 |
| Compound of Example 71 | 1.1 |
| Compound of Example 72 | 0.17 |
| Compound of Example 73 | 1.3 |

As shown in Table 1, the compounds of the invention showed a similar or even stronger ability to induce the cell differentiation as compared with maxacalcitol and it is apparent that they exhibit an excellent vitamin $D_3$ activity.

Test Example 2

Investigation of the Action to Increase Calcium Concentration in Serum

The compound of the invention mentioned in Example 1 or maxacalcitol in ethanol containing 0.3% DMSO was repeatedly subjected to percutaneous administration (33 μg/200 μL/kg/day) once a day for 7 days onto the back of SD male rats (7 weeks of age). Ethanol containing 0.3% DMSO was administered to a control group. At 24 hours after the final administration, blood was collected and the calcium concentration in serum was measured. The result is shown in Table 2.

TABLE 2

| Test Compound | Serum Calcium Concentration (mg/dL) |
|---|---|
| Control | 11.5 |
| Compound of Example 1 | 11.8 |
| Maxacalcitol | 15.0 |

As shown in Table 2, maxacalcitol increased the calcium concentration in serum while the compound of the present invention hardly affected the calcium concentration in serum.

Test Example 3

Investigation of the Action to Increase the Urinary Excretion of Calcium (1)

The compound of the invention mentioned in Example 1, 36, 43, 47, 48, 55 or 70 or maxacalcitol in ethanol containing 0.5% DMSO was repeatedly subjected to a percutaneous administration (10 μg/200 μL/kg/day) once a day for 4 days onto the back of SD male rats (7 weeks of age). Ethanol containing 0.5% DMSO was administered to a control group. The calcium concentration in urine collected every 24 hours was measured and multiplied by the amount of urine to calculate the urinary excretion of calcium. The result is shown in Table 3. The calcium excretion in urine shown in Table 3 indicates the accumulated calcium excretion from 0 to 24 hours, from 0 to 48 hours, from 0 to 72 hours, and from 0 to 96 hours.

TABLE 3

| Test Compound | Calcium in Urine within 24 hours (mg) | Calcium in Urine within 48 hours (mg) | Calcium in Urine within 72 hours (mg) | Calcium in Urine within 96 hours (mg) |
|---|---|---|---|---|
| Control | 1.0 | 1.5 | 2.0 | 2.7 |
| Maxacalcitol | 2.6 | 4.5 | 8.5 | 13.9 |
| Compound of Example 1 | 0.8 | 1.4 | 2.3 | 3.8 |
| Compound of Example 36 | 1.0 | 1.7 | 2.8 | 4.5 |
| Compound of Example 43 | 1.2 | 1.9 | 3.3 | 4.6 |
| Compound of Example 47 | 1.2 | 1.8 | 2.7 | 3.7 |
| Compound of Example 48 | 1.1 | 1.9 | 3.5 | 5.2 |
| Compound of Example 55 | 1.1 | 2.0 | 3.4 | 4.8 |
| Compound of Example 70 | 1.4 | 1.9 | 2.7 | 3.7 |

As shown in Table 3, the calcium level in the urine from the rats of the group administered with the compound of the invention was significantly lower than that from the group administered with maxacalcitol.

Test Example 4

Investigation of the Action to Increase the Urinary Excretion of Calcium (2)

The compound of the invention mentioned in Example 42, 61 or 66, or maxacalcitol in saline containing 0.1% Triton X 100/5.6% DMSO (22.4 nmol/kg) was subjected to an intravenous administration to SD male rats (7 weeks of age) Saline containing 0.1% Triton X 100/5.6% DMSO was administered to a control group. The calcium concentration in urine collected within 24 hours after the administration was measured and the urinary excretion of calcium ([calcium concentration in urine]×[amount of urine]) and the ratio of urinary excretion of calcium based on the control group ([calcium amount in urine in administration of the test compound]/[calcium amount in urine in the control group]) were calculated. The result is shown in Table 4.

TABLE 4

| Test Compound | Calcium in Urine (mg) | Ratio of Calcium in Urine (to control) |
|---|---|---|
| Control | 0.5 | — |
| Maxacalcitol | 2.3 | 460% |
| Compound of Example 42 | 0.8 | 160% |
| Compound of Example 61 | 0.6 | 120% |
| Compound of Example 66 | 0.5 | 100% |

As shown in Table 4, the influence of the compound of the invention on the calcium level in urine was significantly low in the group to which the compound of the invention had been administered, as compared with that in the group administered with maxacalcitol.

Test Example 5

Investigation of Metabolic Rate in Human Liver Microsome

The compounds of the invention mentioned in Examples and maxacalcitol were compared with each other with respect to the metabolic rate in human liver microsome.

As to the pooled human liver microsome (HHM-0323), those manufactured by Tissue Transformation Technologies were used. A 0.25 M potassium phosphate buffer (pH 7.4) (200 µL), 5 µL of a 250 µM solution of each compound to be tested in DMSO, 50 µL of an NADPH-regenerating system (where 20 mg of β-NADP$^+$, 70 mg of glucose-6-phosphate, 40 units of glucose-6-phosphate dehydrogenase and 20 mg of magnesium chloride were dissolved in 1 mL of distilled water) and 220 µL of distilled water were added to a microtube and the mixture was subjected to a preincubation for 5 minutes at 37° C. Reaction was started by an addition of 25 µL of human liver microsome (final concentration of protein: 1 mg/mL). Incubation was performed for 2, 10, 30 or 60 minutes and the reaction was stopped by an addition of 500 µL of acetonitrile. After centrifugation at 13,000 rpm for 5 minutes, each test compound in the supernatant (25 µL) was measured by HPLC under the following conditions.

Inertsil ODS-3 (4.6×150 mm; GL Science) was used as a column. With regard to the mobile phase, a solution A (acetonitrile/0.1% aqueous solution of ammonium acetate=10/90) and a solution B (acetonitrile/0.1% aqueous solution of ammonium acetate=90/10) were used under the linear gradient conditions mentioned in Tables 5 to 7. The column temperature, the flow rate and the wavelength for detection were set at 40° C., 1.0 mL/min. and UV 250 or 270 nm, respectively.

The compound mentioned in Example 38 was analyzed under the condition shown in Table 6; the compounds mentioned in Examples 55, 56, 68, 69, 72 and 73 were under the condition shown in Table 7; and the other compounds were under the condition shown in Table 5.

The compounds described in Examples 40, 43 to 48, 50, 55, 56, 58, 60, 61, 63 and 65 to 73 were analyzed under the condition of UV 250 nm; and the other compounds were under the condition of UV 270 nm.

TABLE 5

| Time (min) | Solution A (%) | Solution B (%) |
|---|---|---|
| 0 | 55 | 45 |
| 10 | 10 | 90 |
| 10.01 | 55 | 45 |
| 16 | Test finished. | |

TABLE 6

| Time (min) | Solution A (%) | Solution B (%) |
|---|---|---|
| 0 | 55 | 45 |
| 10 | 10 | 90 |
| 12 | 10 | 90 |
| 12.01 | 55 | 45 |
| 18 | Test finished. | |

TABLE 7

| Time (min) | Solution A (%) | Solution B (%) |
|---|---|---|
| 0 | 50 | 50 |
| 6 | 10 | 90 |
| 6.01 | 50 | 50 |
| 11 | Test finished. | |

From the HPLC test results as above, the metabolic rate of the test compound was calculated. The result is shown in Table 8.

TABLE 8

| Test Compound | Metabolic Rate (pmol/min/mg) |
|---|---|
| Maxacalcitol | 10 |
| Compound of Example 1 | 78 |
| Compound of Example 3 | 22 |
| Compound of Example 8 | 38 |
| Compound of Example 10 | 58 |
| Compound of Example 13 | 38 |
| Compound of Example 20 | 39 |
| Compound of Example 34 | 36 |
| Compound of Example 35 | 43 |
| Compound of Example 36 | 82 |
| Compound of Example 37 | 36 |
| Compound of Example 38 | 33 |
| Compound of Example 39 | 26 |
| Compound of Example 40 | 65 |
| Compound of Example 41 | 46 |
| Compound of Example 42 | 34 |
| Compound of Example 43 | 74 |
| Compound of Example 44 | 95 |
| Compound of Example 45 | 40 |
| Compound of Example 46 | 45 |
| Compound of Example 47 | 95 |
| Compound of Example 48 | 69 |
| Compound of Example 50 | 45 |
| Compound of Example 55 | 128 |
| Compound of Example 56 | 102 |
| Compound of Example 58 | 29 |
| Compound of Example 60 | 78 |
| Compound of Example 61 | 188 |
| Compound of Example 62 | 24 |
| Compound of Example 65 | 29 |
| Compound of Example 66 | 116 |
| Compound of Example 67 | 38 |
| Compound of Example 68 | 126 |
| Compound of Example 69 | 86 |
| Compound of Example 70 | 60 |

TABLE 8-continued

| Test Compound | Metabolic Rate (pmol/min/mg) |
|---|---|
| Compound of Example 71 | 40 |
| Compound of Example 72 | 111 |
| Compound of Example 73 | 63 |

As shown in Table 8, it is obvious that the compounds of the invention are more rapidly metabolized in human liver microsome than maxacalcitol.

Formulation Example 1

Ointment (1 g) is prepared from 0.25 μg of the compound of Example 1, an ointment base (white Vaseline, medium-chain fatty acid triglyceride, lanoline, paraffin or a mixed base thereof) and other appropriate additives by means of kneading or the like according to a conventional method.

Formulation Example 2

Ointment (1 g) is prepared from 0.25 μg of the compound of Example 2, an ointment base (white Vaseline, medium-chain fatty acid triglyceride, lanoline, paraffin or a mixed base thereof) and other appropriate additives by means of kneading or the like according to a conventional method.

Industrial Applicability

As described in the above, the compound of the invention is a novel useful vitamin $D_3$ derivative, which has an excellent vitamin $D_3$ activity and, as compared with conventional vitamin $D_3$ derivatives, has a relatively small amount of influence on the systemic calcium metabolism.

The invention claimed is:

1. A 9,10-secopregnane compound of formula [1]:

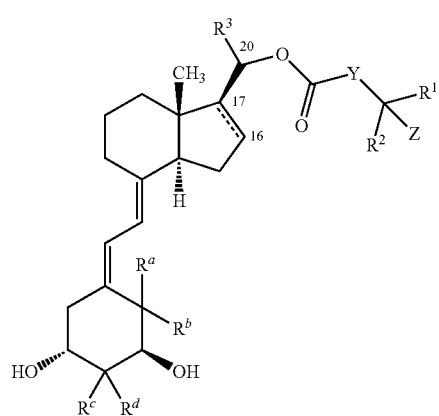

wherein the following partial structure between the 16-position and the 17-position means a single bond or a double bond:

Z is hydroxy, Y is ethylene or ethenylene, $R^1$ and $R^2$ are the same or different, each is methyl, trifluoromethyl or ethyl, and $R^3$ is methyl:

$R^a$ and $R^b$ are both hydrogens, or Ra and $R^b$, taken together, form methylene;

$R^c$ and $R^d$ are the same or different, and each represents hydrogen or methyl, or $R^c$ and $R^d$, taken together, form methylene:

or a pharmaceutically acceptable salt thereof.

2. The 9,10-secopregnane compound or the pharmaceutically acceptable salt thereof as claimed in claim 1, which is a compound of the following (1) to (16):
  (1) (1S,3R,20S)-20-(4-hydroxy-4-methylpentanoyloxy)-9,10-secopregna-5Z,7E,10(19),16-tetraene-1,3-diol,
  (2) (1R,3R,20S)-19-nor-20-(4-hydroxy-4-methylpentanoyloxy)-9,10-secopregna-5Z,7E-diene-1,3-diol,
  (3) (1R,3R,20S)-2-methylene-19-nor-20-(4-hydroxy-4-methylpentanoyloxy)-9,10-secopregna-5Z,7E-diene-1,3-diol,
  (4) (1R,3R,20S)-19-nor-20-[(2E)-4-ethyl-4-hydroxyhex-2-enoyloxy]-9,10-secopregna-5Z,7E-diene-1,3-diol,
  (5) (1R,3R,20S)-19-nor-20-(5,5,5-trifluoro-4-hydroxy-4-methylpentanoyloxy)-9,10-secopregna-5Z,7E-diene-1,3-diol,
  (6) (1R,3R,20S)-2-methylene-19-nor-20-(5,5,5-trifluoro-4-hydroxy-4-methylpentanoyloxy)-9,10-secopregna-5Z,7E-diene-1,3-diol,
  (7) (1R,3R,20S)-2-methylene-19-nor-20-[(2E)-4-ethyl-4-hydroxyhex-2-enoyloxy]-9,10-secopregna-5Z,7E-diene-1,3-diol,
  (8) (1R,3R,20S)-19-nor-20-(4-hydroxy-4-methylpentanoyloxy)-9,10-secopregna-5Z,7E,16-triene-1,3-diol,
  (9) (1R,3R,20S)-19-nor-20-(5,5,5-trifluoro-4-hydroxy-4-methylpentanoyloxy)-9,10-secopregna-5Z,7E,16-triene-1,3-diol,
  (10) (1R,3R,20S)-19-nor-2-methylene-20-(4-hydroxy-4-methylpentanoyloxy)-9,10-secopregna-5Z,7E,16-triene-1,3-diol,
  (11) (1S,3R,20S)-20-(5,5,5-trifluoro-4-hydroxy-4-methylpentanoyloxy)-9,10-secopregna-5Z,7E,10(19),16-tetraene-1,3-diol,
  (12) (1R,2α,3R,20S)-2-methyl-19-nor-20-(4-hydroxy-4-methylpentanoyloxy)-9,10-secopregna-5Z,7E-diene-1,3-diol,
  (13) (1R,2β,3R,20S)-2-methyl-19-nor-20-(4-hydroxy-4-methylpentanoyloxy)-9,10-secopregna-5Z,7E-diene-1,3-diol,
  (14) (1R,3R,20S)-2-methyl-19-nor-20-(5,5,5-trifluoro-4-hydroxy-4-methylpentanoyloxy)-9,10-secopregna-5Z,7E-diene-1,3-diol,
  (15) (1R,3R,20S)-2-methyl-19-nor-20-[(2E)-4-ethyl-4-hydroxyhex-2-enoyloxy]-9,10-secopregna-5Z,7E-diene-1,3-diol,
  (16) (1R,3R,20S)-19-nor-2-methyl-20-(4-hydroxy-4-methylpentanoyloxy)-9,10-secopregna-5Z,7E,16-triene-1,3-diol.

3. A pharmaceutical composition, comprising a 9,10-secopregnane compound or a pharmaceutically acceptable salt thereof of claim 1 and a pharmaceutically acceptable carrier.

4. A method of treating dyskeratosis, which comprises administering an effective amount of a 9,10-secopregnane compound or a pharmaceutically acceptable salt thereof of claim 1 to a patient in need thereof.

5. A method of treating psoriasis vulgaris, which comprises administering an effective amount of a 9,10-secopregnane compound or a pharmaceutically acceptable salt thereof of claim 1 to a patient in need thereof.

* * * * *